United States Patent [19]

Angerbauer et al.

[11] Patent Number: 4,632,918
[45] Date of Patent: Dec. 30, 1986

[54] NOVEL β-LACTAM ANTIBIOTICS

[75] Inventors: Rolf Angerbauer; Michael Boberg; Karl G. Metzger, all of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 730,979

[22] Filed: May 6, 1985

[30] Foreign Application Priority Data

May 22, 1984 [DE] Fed. Rep. of Germany ....... 3419012

[51] Int. Cl.$^4$ ................. A61K 31/545; C07D 501/46
[52] U.S. Cl. ..................................... 514/202; 540/222
[58] Field of Search ........................... 544/22; 514/202

[56] References Cited

U.S. PATENT DOCUMENTS

| 4,416,880 | 11/1983 | Boberg | 544/29 |
| 4,457,929 | 7/1984 | Kamachi | 544/22 |
| 4,525,473 | 6/1985 | Aburaki | 544/22 |

FOREIGN PATENT DOCUMENTS

| 48954 | 4/1982 | European Pat. Off. | 544/22 |
| 82498 | 6/1983 | European Pat. Off. | 544/22 |
| 2076801 | 12/1981 | United Kingdom | 544/22 |

OTHER PUBLICATIONS

Dunn, J. Antimicrobial Chemotherapy (1982), Supple. C, pp. 1–10.

Primary Examiner—Christine M. Nucker
Assistant Examiner—Robert Benson
Attorney, Agent, or Firm—Sprung Horn Kramer & Woods

[57] ABSTRACT

Novel β-lactam antibiotics of the formula

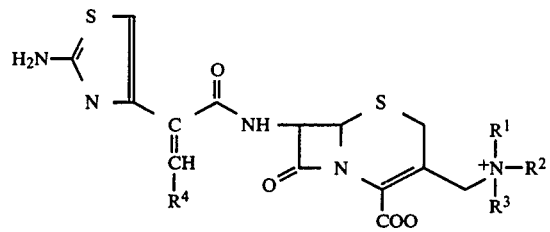

in which
$R^1$, $R^2$ and $R^3$, which may be identical or different, denote a substituted or unsubstituted alkyl radical or a monocyclic or bicyclic, optionally substituted, carbocyclic or heterocyclic ring, or
$R^1$ represents an optionally substituted alkyl radical or a monocyclic or bicyclic, substituted or unsubstituted, carbocyclic or heterocyclic ring, and
$R^2$ and $R^3$, together with the $N^\oplus$ atom, form an optionally substituted monocyclic or polycyclic ring which can be saturated or unsaturated and can contain oxygen, sulphur and nitrogen as other hetero atoms, or
$R^1$, $R^2$ and $R^3$, together with the $N^\oplus$ atom, form a bridged, optionally substituted polycyclic ring which can be saturated or unsaturated and can contain oxygen, sulphur and nitrogen as other hetero atoms, and
$R^4$ represents hydrogen or optionally substituted alkyl, aryl or heterocyclyl or hydroxycarbonyl, lower alkoxycarbonyl, halogen, pseudohalogen or a group of the formula

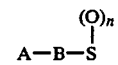

in which
n denotes 0, 1 or 2, and
B represents a direct bond, oxygen or a group

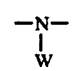

and A and W, independently of one another, represent hydrogen or optionally substituted alkyl, aryl or heterocyclyl, or together form an optionally substituted carbocyclic or heterocyclic ring.

13 Claims, No Drawings

NOVEL β-LACTAM ANTIBIOTICS

The invention relates to β-lactam compounds, to a process for their preparation and to their use as medicaments, in particular as antibacterial agents and, furthermore, as agents for promoting growth and for improving feed utilization in livestock, and as antioxidants.

Cephalosporins which carry as the acyl side-chain an aminothiazolylacrylic acid radical are disclosed in European Pat. No. A 49,448.

The invention makes available new β-lactam compounds which correspond to the general formula (I)

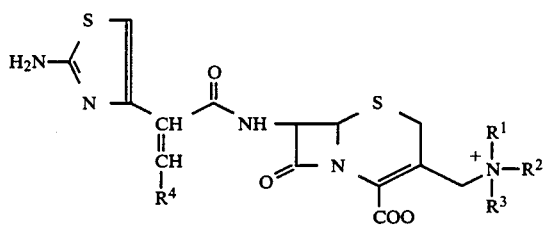

in which
R$^1$, R$^2$ and R$^3$, which may be identical or different, denote a substituted or unsubstituted alkyl radical or a monocyclic or bicyclic, optionally substituted, carbocyclic or heterocyclic ring, or R$^1$ represents an optionally substituted alkyl radical or a monocyclic or bicyclic, substituted or unsubstituted, carbocyclic or heterocyclic ring, and R$^2$ and R$^3$, together with the N atom, form an optionally substituted monocyclic or polycyclic ring which can be saturated or unsaturated and can contain oxygen, sulphur and nitrogen as other hetero atoms, or R$^1$, R$^2$ and R$^3$, together with a N atom, form a bridged, optionally substituted polycyclic ring which can be saturated or unsaturated and can contain oxygen, sulphur and nitrogen as other hetero atoms, and R$^4$ represents hydrogen or optionally substituted alkyl, aryl or heterocyclyl or hydroxycarbonyl, lower alkoxycarbonyl, halogen, pseudohalogen or a group of the formula (II)

in which
n denotes 0, 1 or 2, and
B represents a direct bond, oxygen or a group

and A and W, independently of one another, represent hydrogen or optionally substituted alkyl, aryl or heterocyclyl, or together form an optionally substituted carbocyclic or heterocyclic ring. The meaning of alkyl comprises in each case straight-chain or branched, optionally substituted radicals having up to 18 C atoms, particularly preferably having up to 10 C atoms, and specifically having up to 6 C atoms, which can also be unsaturated, preferably having 1 or 2 double bonds, and carbocyclic.

In the compounds of the formula (I), there exists for each structural formula one compound having the E and one having the Z configuration in accordance with the E/Z nomenclature described in J. Amer. Chem. Soc. 90, 509 (1968).

Preferred compounds of the formula I are in the Z configuration.

Preferred compounds in which R$^4$ has the abovementioned meaning, and
R$^1$, R$^2$ and R$^3$ are identical or different and represent an optionally substituted C$_1$-C$_6$-alkyl radical or a 3- to 7-membered optionally substituted ring, or R$^1$ has the abovementioned meaning, and
R$^2$ and R$^3$, together with the N atom, form a 3-7-membered ring which can be saturated or unsaturated and can be substituted by one or more, preferably 1-3, identical or different substituents and can contain one or two other hetero atoms which can be oxygen, nitrogen and/or sulphur.

Within the scope of this definition, alkyl also comprises unsaturated and carbocyclic radicals.

When R$^1$ and/or R$^2$ and/or R$^3$ represent a substituted alkyl radical, then it preferably has one or two substituents, preferably hydroxyl, carboxyl, C$_1$-C$_6$-alkyloxycarbonyl, formyl or C$_1$-C$_6$-alkylcarbonyl, whose carbonyl groups can also be in the ketalized form, carbonyl, sulpho, cyano, nitro, amino, halogen, C$_1$-C$_6$-alkylamino and dialkylamino, C$_1$-C$_6$-alkylcarbonylamino, C$_1$-C$_6$-alkyloxy, C$_1$-C$_6$-alkylthio, C$_1$-C$_6$-alkylsulphinyl, C$_1$-C$_6$-alkylsulphonyl, aryl, hetaryl or heterocyclyl.

When R$^1$ and/or R$^2$ and/or R$^3$ represent a saturated or unsaturated, optionally substituted, 3- to 7-membered ring, then it is preferably a carbocyclic or heterocyclic ring which can contain up to three, preferably one or two, hetero atoms which can be oxygen, nitrogen and/or sulphur.

If the ring is substituted, then this is preferably with one or two substituents, preferably C$_1$-C$_6$-alkyl, hydroxyl, hydroxy-C$_1$-C$_6$-alkyl, carboxyl, C$_1$-C$_6$-alkyloxycarbonyl, formyl or C$_1$-C$_6$-alkylcarbonyl, whose carbonyl groups can also be in the ketalized form, carbamoyl, sulpho, cyano, nitro, amino, halogen, C$_1$-C$_6$-alkylamino and dialkylamino, C$_1$-C$_6$-alkylcarbonylamino, C$_1$-C$_6$-alkyloxy, C$_1$-C$_6$-alkylthio, C$_1$-C$_6$-alkylsulphinyl, C$_1$-C$_6$-alkylsulphonyl, aryl, hetaryl or heterocyclyl.

When R$^2$ and R$^3$, together with the N atom, form an optionally substituted heterocyclic ring, then it is preferably a 3- to 7-membered ring which can contain one or two double bonds and up to two other hetero atoms which can be oxygen, nitrogen or sulphur, and onto which another 5- to 6-membered ring can be fused.

When the heterocyclic ring formed by R$^2$ and R$^3$ together with the N atom is substituted, then this is preferably with one or two substituents, preferably optionally substituted C$_1$-C$_6$-alkyl, hydroxyl, hydroxy-C$_1$-C$_6$-alkyl, carboxyl, C$_1$-C$_6$-alkyloxycarbonyl, formyl or C$_1$-C$_6$-alkylcarbonyl, whose carbonyl groups can also be in the ketalized form, carbamoyl, sulpho, cyano, nitro, amino, halogen, C$_1$-C$_6$-alkylamino and dialkylamino, C$_1$-C$_6$-alkylcarbonylamino, C$_1$-C$_6$-alkyloxy, C$_1$-C$_6$-alkylthio, C$_1$-C$_6$-alkylsulphinyl, C$_1$-C$_6$-alkylsulphonyl, aryl, hetaryl or heterocyclyl.

When R$^4$ represents an alkyl radical, then it is preferably a straight-chain or branched, optionally substituted radical having up to 18 C atoms, particularly preferably having up to 12 C atoms, and specifically having up to 6 C atoms. Within the scope of this definition, alkyl also comprises unsaturated radicals, preferably having 1 or 2 double bonds, and carbocyclic radicals.

When the alkyl radical $R^4$ is substituted, then this is preferably with one or two substituents, preferably from the group comprising halogen, preferably F, Cl or Br, OH, lower alkoxy, oxo, thio, nitro, cyano, hydroxycarbonyl, lower alkoxycarbonyl, aminocarbonyloxy, sulpho, aryl, —O—COR$^5$,

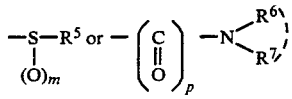

in which
  m denotes 0, 1 or 2,
  p denotes 0 or 1,
  $R^5$ represents lower alkyl or aryl, preferably phenyl, and
  $R^6$ and $R^7$, independently of one another, represent hydrogen, lower alkyl or lower alkanoyl, or together represent lower alkylene.

The meaning of alkyl in each case also comprises substituted and/or cyclic and/or unsaturated structures.

When $R^4$ represents an aryl radical, then it is preferably a radical of the formula

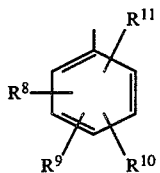

in which
  $R^8$, $R^9$, $R^{10}$ and $R^{11}$, independently of one another denote hydrogen, halogen, preferably F, Cl or Br, optionally substituted lower alkyl, aryl, a group —OCOR$^{12}$, a group

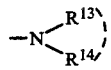

nitro, cyano, lower alkoxy, lower alkylthio, hydroxycarbonyl, lower alkoxycarbonyl, aminocarbonyloxy, hydroxycarbonyl-C$_1$-C$_6$-alkyl, lower alkoxycarbonyl-C$_1$-C$_6$-alkyl, sulphonyl or sulpho, in which in turn aryl denotes a substituted or unsubstituted carbocyclic aromatic ring, preferably phenyl or a 5- or 6-membered heterocyclic ring,
and in which
  $R_{12}$ denotes lower alkyl,
and in which
  $R^{13}$ and $R^{14}$, independently of one another, can be hydrogen, lower alkyl or lower alkanoyl, or together represent lower alkylene.

When $R^4$ represents a heterocyclic radical, then it is preferably a 5- or 6-ring with 1–4 hetero atoms, identical or different, from the group comprising N, O and S. The pyridine, pyrimidine, pyrazine, pyridazine, furan, thiophene, isoxazole or thiazole radicals are very particularly preferred.

Preferred substituents on a heterocyclic radical of this definition are lower alkyl, aryl, halogen, preferably F, Cl or Br, a group —OCOR$^{12}$, lower alkoxy, lower alkylthio, nitro, cyano, a group

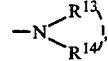

hydroxycarbonyl, lower alkoxycarbonyl, aminocarbonyloxy, sulphonyl or sulpho, in which aryl in turn denotes a substituted or unsubstituted carbocyclic aromatic ring, preferably phenyl, or a 5- or 6-membered heterocyclic ring, and in which $R^{12}$, $R^{13}$ and $R^{14}$ have the abovementioned meaning.

Very particularly preferred compounds of the formula I are those in the Z configuration
in which
  $R^1$, $R^2$ and $R^3$ are identical or different and represent a C$_1$-C$_6$-alkyl radical, such as, in particular, methyl, ethyl, propyl, cyclopropyl, cyclopropylmethyl, cyclopentyl or cyclopentylmethyl, or a substituted C$_1$-C$_6$-alkyl radical, such as, in particular, hydroxymethyl, hydroxyethyl, hydroxypropyl, aminomethyl, aminoethyl, hydroxycarbonylmethyl, hydroxycarbonylethyl, cyanomethyl, nitromethyl, nitroethyl, methoxymethyl, methoxycarbonylmethyl or trifluoromethyl, or in which
  $R^1$ has the abovementioned meaning, and
  $R^2$ and $R^3$, together with the N atom, form a 5- or 6-membered heterocyclic ring which can contain another hetero atom and onto which another ring can be fused, such as, in particular, pyrrolidinium, piperidinium, morpholinium, pyrrolinium, pyrazolidinium, indolinium, isoindolinium, oxazolidinium, thiazolidinium, thiomorpholinium and which can be optionally substituted by C$_1$-C$_6$-alkyl, such as, in particular, methyl, ethyl or propyl, which in turn can be substituted by, for example, hydroxyl, carboxyl, cyano, nitro, amino, halogen, alkoxy, by C$_1$-C$_6$-alkoxycarbonyl such as methoxycarbonyl, formyl or C$_1$-C$_6$-alkylcarbonyl such as, in particular, methylcarbonyl and ethylcarbonyl, by carbamoyl, sulpho, cyano, nitro, halogen such as, in particular, fluoride and chloride, amino, C$_1$-C$_6$-alkylamino and dialkylamino such as, in particular, methylamino and diethylamino, C$_1$-C$_6$-alkylcarbonylamino such as, in particular, methylcarbonylamino and ethylcarbonylamino, C$_1$-C$_6$-alkyloxy such as, in particular, methoxy, C$_1$-C$_6$-alkylthio such as, in particular, methylthio, C$_1$-C$_6$-alkylsulphinyl such as, in particular, methylsulphinyl, C$_1$-C$_6$-alkylsulphonyl, such as, in particular, methylsulphonyl and ethylsulphonyl, by aryl such as, in particular, phenyl or naphthyl, which can also be substituted, by hetaryl such as pyridyl, which can also be substituted, and
  $R^4$ denotes a lower alkyl radical, such as methyl, ethyl, propyl, alkyl, cyclopropyl or cyclopentyl, an unsubstituted or substituted aryl radical, such as phenyl, dichlorophenyl, trichlorophenyl, hydroxycarbonylphenyl or hydroxycarbonyl-C$_1$-C$_6$-alkylphenyl, a heterocyclic 5- or 6-ring, such as pyridyl or aminothiazolyl, hydroxycarbonyl, hydroxycarbonyl-C$_1$-C$_4$-alkyl, such as 1-hydroxycarbonyl-1-methylethyl, lower alkoxycarbonyl, such as methoxycarbonyl, or $C_1$-$C_4$-alkylsulphonyl, such as methylsulphonyl.

Furthermore, the invention makes available new β-lactam compounds of the general formula IV in which $R_1$, $R_2$ and $R_3$ have the same meaning as in formula I, which can be used as intermediates for the preparation of the compounds of the formula I.

The compounds of the general formula I can be obtained by reacting compounds of the general formula (III)

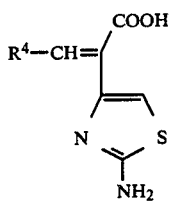

in which $R^4$ has the abovementioned meaning,
in which the amino group can be in the protected or unprotected form, after activation of the carboxyl group by conversion into a mixed anhydride, for example with ethyl chloroformate or methanesulphonyl chloride, after conversion into the acid halide or after conversion into an activated ester with, for example, N-hydroxybenzotriazole and dicyclohexylcarbodiimide, with compounds of the general formula (IV)

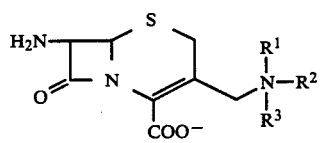

in which $R^1$, $R^2$ and $R^3$ have the abovementioned meaning,
then, where appropriate, eliminating protecting groups, and preparing the desired salts or from salts the free acids.

A large number of methods known from cephalosporin and penicillin chemistry can be used for coupling carboxylic acids (III) to β-lactams of the formula IV. It has proved to be advantageous to activate the carboxylic acids of the general formula III without an amine protecting group and then to couple them with the β-lactams of the formula IV, which have been induced to dissolve as salts with an amine. It is particularly advantageous to activate with sulphonic acid derivatives of the formula (V) to give anhydrides of the formula VI

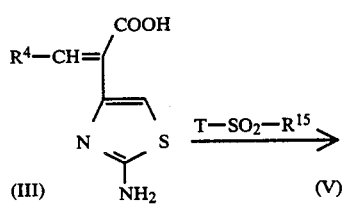

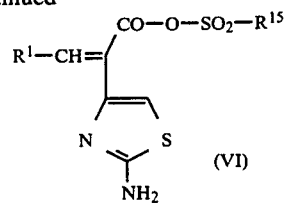

in which
T represents a radical $R^{15}$—$SO_2O$ or halogen, and
$R^{15}$ denotes an alkyl radical having 1-10 C atoms which can optionally be substituted by fluorine, chlorine, CN, phenyl, alkyloxycarbonyl, alkyloxy or alkyl, it being possible for the latter alkyl radicals to bear 1-4 C atoms, or a phenyl radical which can optionally be substituted by fluorine, chlorine, bromine, CN, alkyl, alkyloxy, alkylthio, alkylcarbonyl—it being possible for the latter alkyl groups to bear 1-4 C atoms—nitro, trifluoromethyl and phenyl. When $R^{15}$ is substituted, then there are preferably 1-3 substituents present, preferably those mentioned.

$R^{15}$ very particularly preferably represents a methyl or p-tolyl radical.

The mixed anhydrides of the formula VI are prepared by dissolving the carboxylic acids of the formula III and 1–1.4 equivalents of an amine in a solvent and allowing them to react with 1 to 1.2 equivalents of a sulphonic acid derivative of the formula V.

Suitable solvents are all solvents which are stable under the reaction conditions, such as, for example, diethyl ether, tetrahydrofuran, acetonitrile, acetone, methylene chloride, chloroform or dimethylformamide.

Suitable amines are tertiary amines, such as, for example triethylamine or tributylamine, as well as sterically hindered secondary amines, such as, for example, diisopropylamine.

The reactions can be carried out at temperatures between −80° C. and room temperature, low temperatures preventing isomerization of the substituents on the double bond. The activation is advantageously carried out with Cl—$SO_2CH_3$ in dimethylformamide, at −40° to −60° C., within 0.2 to 24 hours, preferably 0.5 to 5 hours.

It is possible to use to dissolve the compounds of the formula IV the solvents mentioned for the preparation of the compounds of the formula VI, and to use as base the amines mentioned there.

It is also particularly advantageous to activate the carboxylic acids of the general formula III by conversion into an activated ester with, for example, N-hydroxysuccinimide and dicyclohexylcarbodiimide or 1-hydroxybenzotriazole and dicyclohexylcarbodiimide.

Suitable solvents are all solvents which are also suitable for the preparation of anhydrides of the formula VI.

The reactions can be carried out at temperatures between −30° and +100°. Activation is advantageously carried out with 1-hydroxybenzotriazole and dicyclohexylcarbodiimide in dimethylformamide for 2 to 6 hours at room temperature, then the precipitated dicyclohexylurea is filtered off with suction and the reaction is carried out with a compound of the formula IV in the form of a solution of its amine salt, within 2 to 24 hours. It is possible to use to dissolve the compounds of the formula IV the solvents mentioned for the preparation of the compounds of the formula VI, and to use as base the amines mentioned there.

The compounds of the formula IV are obtained by eliminating the amine protecting group $R^{16}$ from compounds of the formula VII. In this connection, $R^{16}$ can be either an acid-labile protecting group

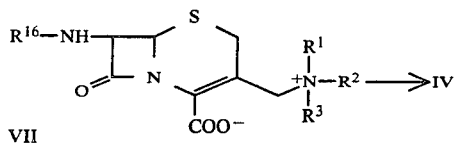
VII such as the t-butyloxycarbonyl group or, advantageously, a protecting group which can be eliminated enzymatically. Preferred protecting groups which can be eliminated enzymatically are phenacetyl or 2-thienylacetyl. The enzymatic elimination is carried out at room temperature, in water or a mixture of water and a polar organic solvent, such as, for example, acetonitrile or tetrahydrofuran, using immobilized penicillin-G acylase at pH 7-8, preferably at pH 7.5-7.8. During the elimination, the pH is kept constant by addition of a base, such as lithium hydroxide, sodium hydroxide, potassium hydroxide or a tertiary amine, for example triethylamine, tripropylamine, tributylamine or pyridine.

The compounds of the formula VII can be prepared from esters of the formula VIII via intermediate compounds of the formula IX.

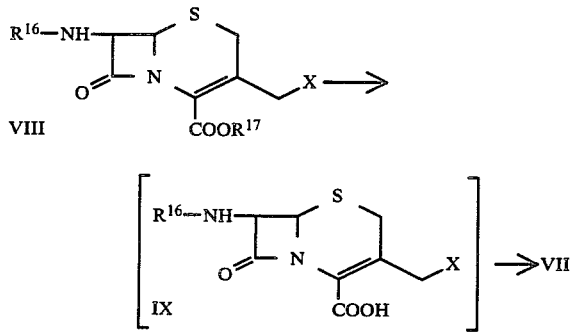

In the esters of the formula VIII, X represents a leaving group, such as mesylate, tosylate, brosylate, triflate, nonaflate, iodide, bromide or chloride, and $R^{17}$ represents an acid protecting group customary in cephalosporin chemistry, preferably a protecting group which can be eliminated by acid, such as, for example, benzhydryl, 4-methoxydiphenylmethyl or t-butyl.

The compounds of the formula VIII are converted into the reactive free acids of the formula IX by elimination of the acid protecting group $R^{17}$. With the preferred acid-labile protecting groups $R^{17}$, the protecting group is eliminated in an organic solvent. The elimination of the benzhydryl protecting group is preferably carried out in methylene chloride with trifluoroacetic acid, possibly with the addition of an alkoxybenzene, preferably methoxybenzene. The elimination is carried out at −20° C. to +30° C., preferably at 0° C., within 5 minutes to one hour, preferably within 20 minutes.

The acid of the formula IX can be isolated after the protecting group has been eliminated. However, it is advantageously not isolated but reacted directly and without purification to give compounds of the formula VII. For this purpose, the solution of IX produced in the reaction VIII→IX is concentrated in vacuo under mild conditions. The remaining crude acid is taken up in an organic solvent, preferably in tetrahydrofuran, and reacted with 2-20 equivalents, preferably with 5-10 equivalents, of a tertiary amine of the formula $NR_1R_2R_3$, in which $R^1$, $R^2$ and $R^3$ have the above-mentioned meaning, to give compounds of the formula VII. The reaction is carried out at temperatures between −20° C. and 40° C., preferably at 25° C., within 10 minutes to two hours, preferably within 30 minutes. After the reaction is complete, the product can be precipitated by addition of diethyl ether. The crude product thus obtained can be purified on a resin, such as Diaion HP 20 or XAD 7. It is also possible and advantageous directly to react further the crude product to give compounds of the formula IV.

Alternatively, the compounds of the formula VII can also be prepared from acids of the formula X in which $R^{16}$ has the abovementioned

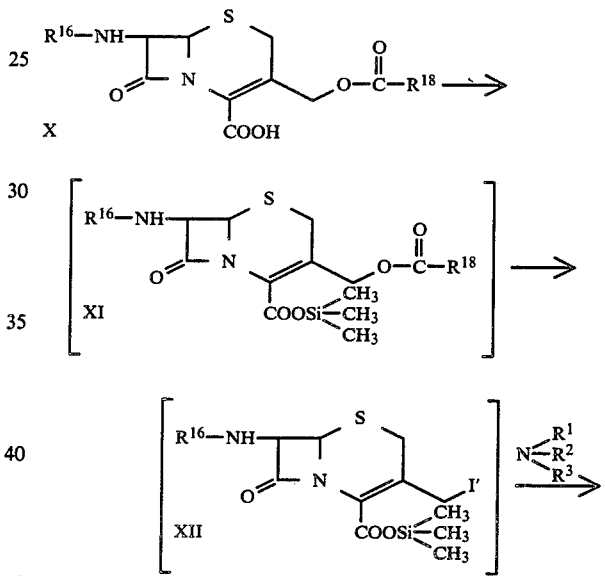

meaning and $R^{18}$ represents an optionally substituted alkyl or aryl such as methyl, ethyl, propyl, chloromethyl, dichloromethyl, trichloromethyl, trifluoromethyl or phenyl. $R^{18}$ very particularly preferably represents a methyl group.

The starting compounds of the formula X are suspended in a suitable organic solvent and induced to dissolve by silylation to give the silyl esters XI. Particularly suitable organic solvents are chloroform, methylene chloride and dichloroethane. The silylation is carried out with a customary silylating agent, such as trimethylchlorosilane (TMCS), hexamethyldisilazane (HMDS), N,O-bis(trimethylsilyl)acetamide (BSA), N,O-bis(trimethylsilyl)trifluoroacetamide (BSTFA), N-methyl-N-trimethylsilylacetamide (MSA), N-methyl-N-trimethylsilyltrifluoroacetamide (MSTFA), 1,3-bis(trimethylsilyl)urea and trimethylsilyl trifluoromethanesulphonate. This may also entail several silylating agents being used in the mixture.

The silylation is carried out at −30° C. to +70° C., preferably at −10° C. to +10° C., within 5 minutes to 30 minutes. It is advantageous to use an excess of up to ten-fold of the silylating agent, preferably an excess of two- to five-fold.

The solution of the trimethylsilyl ester thus obtained, of the formula XI, is reacted, at −40° C. to +30° C. preferably at −10° C. to +10° C., with one to ten equivalents, preferably with three to four equivalents, of a trialkylsilyl iodide, particularly preferably trimethylsilyl iodide, within 15 minutes to 2 hours, preferably within 30 minutes to 1 hour, to give compounds of the formula XII.

It is advantageous not to isolate the compounds of the formula XII but to react them directly, without purification, with amines

to give the compounds of the formula VII.

Alternatively, the compounds of the general formula I can also be prepared by reacting compounds of the formula XIII

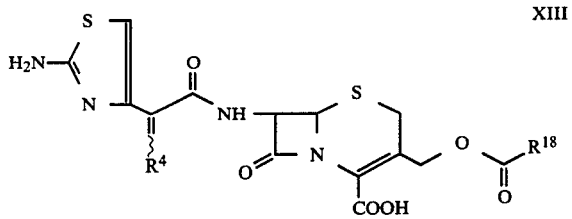

in which $R^4$ and $R^{18}$ have the abovementioned meaning, directly, without isolation of the intermediates, after silylation and conversion into the iodide, with amines

to give compounds of the formula I, in analogy to the reaction of compounds of the formula X to give compounds of the formula VII described previously.

The compounds according to the invention exhibit a potent and broad antimicrobial efficacy, especially for Gram-negative and Gram-positive bacteria. These properties make it possible to use them as chemotherapeutic active compounds in medicine. Using them, it is possible to prevent, ameliorate and/or cure diseases caused by Gram-negative and Gram-positive bacteria and bacteroid microorganisms.

The compounds according to the invention are particularly effective for bacteria and bacteroid microorganisms. Thus, they are particularly well suited for the prophylaxis and chemotherapy of local and systemic infections caused by these pathogens in human and veterinary medicine.

For example, it is possible to treat and/or prevent local and/or systemic diseases caused by the following pathogens or by mixtures of the following pathogens: Micrococcaceae, such as staphylococci, for example *Staphylococcus aureus, Staph. epidermidis, Staph. aerogenes* and *Graffkya tetragena* (Staph. = staphylococcus); Lactobacteriaceae, such as streptococci, for example *Streptococcus pyogenes*, α- and β-haemolytic streptococci, non-(γ-)-haemolytic streptococci, *Str. viridans, Str. faecalis* (enterococci) and *Dipolococcus pneumoniae* (pneumococci) (Str. = streptococcus); Enterobacteriaceae, such as Escherichia bacteria of the coli group: Escherichia bacteria, for example *Escherichia coli*, enterobacter bacteria, for example *E. aerogenes, E. cloacae*, klebsiella bacteria, for example *K. Pneumoniae*, Serratia, for example *Serratia marcescens* (E. = enterobacter) (K. = klebsiella), proteae bacteria of the proteus group: for example *Proteus vulgaris, Pr. morganii, Pr. rettgeri, Pr. mirabilis* (Pr. = proteus); Pseudomonadaceae, such as pseudomonas bacteria, for example *Pseudomonas aeruginosa* (Ps = pseudomonas); Bacteroidaceae, such as bacteroides bacteria, for example *Bacteroides fragilis* (B. = bacteroides).

The above list of pathogens is merely by way of example and is by no means to be regarded as restrictive.

Examples of diseases which can be prevented, ameliorated and/or cured by the compounds according to the invention and which may be mentioned are: diseases of the respiratory tract and of the pharyngeal cavity; otitis; pharyngitis; pneumonia; peritonitis; pyelonephritis; cystitis, endocarditis; systemic infections; bronchitis; arthritis; local infections.

The present invention includes pharmaceutical formulations which, in addition to non-toxic, inert pharmaceutically suitable vehicles, contain one or more compounds according to the invention or which consist of one or more active compounds according to the invention, and processes for the preparation of these formulations.

The present invention also includes pharmaceutical formulations in dosage units. This means that the formulations are in the form of individual parts, for example tablets, coated tablets, capsules, pills, suppositories and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable vehicles there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical formulations.

Tablets, coated tablets, capsules, pills and granules can contain the active compound or compounds alongside the customary vehicles, such as (a) fillers and extenders, for example starches, lactose, sucrose, glucose, mannitol and silica, (b) binders, for example carboxymethylcellulose, alginates, gelatin and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol or glycerol monostearate, (h) adsorbents, for example kaolin and bentonite and (i) lubricants, for example talc, calcium magnesium stearate and solid polyethylene glycols or mixtures of the substances listed under (a) to (i).

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned vehicles, can also be in a microencapsulated form.

Suppositories can contain, in addition to the active compound or compounds, the customary water-soluble or water-insoluble vehicles, for example polyethylene glycols, fats, for example cacao fat, and higher esters for example $C_{14}$-alcohol with $C_{16}$-fatty acid) or mixtures of these substances.

For parenteral administration, these solutions can also be in a sterile form which is isotonic with blood.

The therapeutically active compounds should preferably be present in the abovementioned pharmaceutical formulations in a concentration of about 0.1 to 99.5, preferably about 0.5 to 95, % by weight of the total mixture.

The abovementioned pharmaceutical formulations can also contain other pharmaceutical active compounds in addition to the compounds according to the invention.

The abovementioned pharmaceutical formulations are prepared in the usual manner according to known methods, for example by mixing the active compound or compounds with the vehicle or vehicles.

The active compounds or the pharmaceutical formulations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds in amounts of about 1 to about 1,000, preferably 1 to 200, mg/kg of body weight every 24 hours, optionally in the form of several individual administrations, in order to achieve the desired results. An individual administration contains the active compound or compounds according to the invention preferably in amounts of about 1 to about 250, in particular 1 to 60, mg/kg of body weight. However, it can be necessary to deviate from the dosages mentioned and in particular to do so as a function of the nature and body weight of the subject to be treated, the nature and severity of the illness, the nature of the formulation and of the administration of the medicine, and the time or interval over which administration takes place. Thus, it can suffice in some cases to manage with less than the abovementioned amount of active compound, while in other cases the abovementioned amount of active compound must be exceeded. The particular required optimum dosage and the type of administration of the active compounds can easily be decided by anyone skilled in the art, on the basis of his expert knowledge.

With the object of widening the spectrum of action, the compounds according to the invention can be combined with another β-lactam antibiotic or with aminoglycoside antibiotics, such as, for example, gentamicin, sisomicin, kanamicin, amikacin or tobramicin.

The active compounds according to the invention can be used in all branches of livestock breeding as agents to promote and accelerate growth and to improve the utilization of feed of healthy and diseased livestock.

In this connection, the efficacy of the active compounds is essentially independent of the species and sex of the animals. The active compounds prove to be particularly valuable in the rearing and management of young and fattening livestock. The following useful and ornamental livestock may be mentioned as examples of livestock for which the active compounds can be used for the promotion and acceleration of growth and for the improvement of the utilization of feed:

Warm-blooded species, such as cattle, pigs, horses, sheep, goats, cats, dogs and rabbits; fur-bearing animals, for example mink and chinchilla; poultry, for example chickens, geese, ducks, turkeys, pigeons, parrots and canaries, and cold-blooded species, such as fish, for example carp, and reptiles, for example snakes.

The amounts of the active compounds administered to the livestock to achieve the desired effect can be varied over a wide range because of the favourable properties of the active compounds. It is preferably about 0.01 to 50, in particular 0.1 to 10, mg/kg of body weight per day. The period of administration can be from a few hours or days up to several years. The amount of the active compound to be administered and the appropriate period of administration depend, in particular, on the species, the age, the sex, the state of health and the manner of management and feeding of the livestock, and can be readily determined by those skilled in the art.

The active compounds are administered to the livestock using the customary methods. The mode of administration depends, in particular, on the species, the behaviour and the state of health of the livestock. Thus, the administration can be carried out orally or parenterally, once or several times a day, at regular or irregular intervals. For reasons of convenience, in most cases oral administration, in particular in the rhythm of the intake of food and/or drink by the livestock, is to be preferred. Food in the sense of the present invention is to be understood to include both solid and liquid food as well as beverages and water.

The active compounds can be administered as the pure substances or in a formulated form, that is to say mixed with non-toxic inert vehicles of any desired type, for example with vehicles and in formulations as are customary for nutritive formulations.

The active compounds are administered where appropriate in a formulated form together with pharmaceutically active compounds, mineral salts, trace elements, vitamins, proteins, lipids, colorants and/or flavoring agents in a suitable form.

Oral administration together with the feed and/or drinking water is advisable, either the total amount or only portions of the active compound, depending on requirements, being added to the feed and/or drinking water.

The active compounds are prepared by customary methods by simply mixing as a pure mixture of substances, preferably in a finely divided form, or in a formulated form mixed with edible non-toxic vehicles, where appropriate in the form of a premix or a feed concentrate to which feed and/or drinking water is added.

The feed and/or drinking water can contain, for example, the active compounds in a concentration by weight of about 0.01 to 50, in particular 0.1 to 10, ppm. The optimal level of the concentration of the active compounds in the feed and/or drinking water depends, in particular, on the amount of feed and/or drinking water consumed by the livestock, and can be readily determined by those skilled in the art.

The type of the feed and its composition has no relevance in this context. It is possible to use all conventional or special feed compositions, which preferably contain the customary balance, which is necessary for balanced nutrition, of energy suppliers and building substances, including vitamins and minerals. The feed can be composed of, for example, vegetable materials, for example hay, roots, cereals and cereals by-products, animal materials, for example meat, fats, bonemeal, fish products, vitamins, for example vitamin A, D complex and B complex, proteins, aminoacids, for example DL-methionine, and inorganic materials, for example lime and sodium chloride.

Feed concentrates contain the active compounds in addition to edible materials, for example rye meal, maize meal, soya bean meal or lime, where appropriate with other nutrients and building substances, as well as proteins, mineral salts and vitamins. They can be prepared by the customary mixing methods.

It is also possible, preferably in premixes and feed concentrates, where appropriate to protect the active compounds from air, light and/or moisture by agents suitable for covering their surface, for example with non-toxic waxes or gelatin.

An example of the composition of a chicken rearing feed which contains an active compound according to the invention:

200 g of wheat, 340 g of corn, 361 g of soybean meal, 60 g of beef tallow, 15 g of dicalcium phosphate, 10 g of calcium carbonate, 4 g of iodized sodium chloride, 7.5 g of vitamin/mineral mixture and 2.5 g of active compound premix provide, after thorough mixing, 1 kg of feed.

One kg of feed mixture contains:
600 I.U. of vitamin A, 100 I.U. of vitamin $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

The active compound premix contains the active compounds in the desired amount, for example 10 mg, with the addition of 1 g of DL-methionine and sufficient soybean meal to produce 2.5 g of premix.

An example of the composition of a pig rearing feed which contains an active compound according to the invention: 630 g of ground feed grain (composed of 200 g of corn, 150 g of barley meal, 150 g of oatmeal and 130 g of wheat meal), 80 g of fish meal, 60 g of soybean meal, 60 g of cassava meal, 38 g of brewer's yeast, 50 g of vitamin/mineral mixture for pigs (composition, for example, as for chicken feed), 30 g of ground linseed cake, 30 g of corn gluten, 10 g of soybean oil, 10 g of cane sugar molasses and 2 g of active compound premix (composition, for example, as for chicken feed) provide, after thorough mixing, 1 kg of feed.

The feed mixes indicated are formulated preferably for the rearing and fattening of chickens and pigs respectively, but they can also be used in the same or similar composition for the rearing and fattening of other livestock.

EXAMPLE 1

Benzhydryl 3-chloromethyl-7β-phenylacetamido-3-cephem-4-carboxylate 24 ml (0.3 mol) of pyridine, 400 μl of dimethylformamide and 21.6 ml (0.3 mol) of thionyl chloride are added, while cooling in ice, to a solution of 103 g (0.2 mol) of benzhydryl 3-hydroxymethyl-7β-phenylacetamido-3-cephem-4-carboxylate (prepared according to, for example, Helv. Chim. Acta 57, 2044 (1974)) in 3.5 l of absolute tetrahydrofuran. After 10 minutes, the mixture is evaporated in a rotary evaporator, the residue is taken up in 2 l of ethyl acetate, and the solution is extracted by shaking twice with sodium bicarbonate solution and once with water. The organic phase is stirred with 50 g each of kieselguhr and active charcoal and filtered with suction through a sintered glass funnel containing silica gel. It is then dried over magnesium sulphate, evaporated, and residue is taken up in 200 ml of methylene chloride and the product is precipitated with petroleum ether.

Yield: 76 g $^1$H-NMR (DCCl$_3$)

δ(ppm)=7.20–7.50 (15H, m, arom.); 6.96 (1H, s, CHφ$_2$); 6.30 (1H, d, J=9 Hz, NH); 5.86 (1H, dd, J=9 Hz, J=5 Hz, H-7); 4.95 (1H, d, J=5 Hz, H-6); 4.36 (2H, bs, CH$_2$Cl); 3.66 (1H, d, J=15 Hz, φ—CH$_2$—); 3.58 (1H, d, J=15 Hz, φ—CH$_2$—); 3.56 (1H, d, J=18 Hz, H-2); 3.40 (1H, d, J=18 Hz, H-2).

EXAMPLE 2

3-(1-Methyl-1-pyrrolidinium)methyl-7β-phenylacetamido-3-cephem-4-carboxylate 2.13 g (4 mmol) of benzhydryl 3-chloromethyl-7β-phenylacetamido-3-cephem-4-carboxylate are dissolved in 24 ml of absolute methylene chloride at 0° C. After addition of 12 ml of anisole and 12 ml of trifluoroacetic acid, the mixture is stirred at 0° C. for 25 minutes. It is then evaporated in vacuo, 10 ml of benzene are added, and the mixture is evaporated under high vacuum for 1 h. The residue is dissolved in 20 ml of absolute tetrahydrofuran, and 1.7 g (20 mmol) of N-methylpyrrolidine are added. The solution is stirred at room temperature for 30 minutes. 100 ml of ether are added, and the ether is decanted off. The residue is again stirred with ether, the ether again decanted off, and the residue is briefly dried in vacuo and then suspended in 100 ml of water. It is neutralized with ion exchanger MP 62 and then chromatographed on absorber resin HP 20. (Mobile phase: water/acetonitrile 95/5). The product fractions are then freeze-dried.

Yield: 0.725 g (44%)

$^1$H-NMR (DMSO-d$_6$)

δ(ppm)=9.21 (1H, d, J=9 Hz, NH); 7.25–7.35 (5H, m, arom.); 5.55 (1H, dd, J=9 Hz, J=5 Hz, H-7); 5.07 (1H, d, J=5 Hz, H-6); 5.00 (1H, d, J=13 Hz, CH$_2$—pyrrol.); 3.93 (1H, d, H=13 Hz, CH$_2$—pyrrol); 3.82 (1H, d, H=18 Hz, S—CH$_2$); 3.60 (1H, d, J=14 Hz, φ—CH$_2$); 3.51 (1H, d, J=14 Hz, φ—CH$_2$); 3.42 (4H, m, pyrrol.); 3.34 (1H, d, J=18 Hz, S—CH$_2$; 2.92 (3H, S,

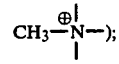

2.06 (4H, m, pyrrol.)

EXAMPLE 3

7-Amino-3-(1-methyl-1-pyrrolidinium)methyl-3-cephem-4-carboxylate 3.32 g (8 mmol) of 3-(1-methyl-1-pyrrolidinium)methyl-7β-phenylacetamido-3-cephem-4-carboxylate are dissolved in 100 ml of water. The pH is adjusted to 7.8 with 4N triethylamine in ethanol. Then 4 g of penicillin-G acylase are added, and the pH is maintained constant by addition of triethylamine. After the enzymatic cleavage is complete, the acylase is filtered off, and the filtrate is adjusted to pH 2 with concentrated hydrochloric acid. The resulting precipitate is filtered off over kieselguhr with suction, and the filtrate is added dropwise to 2 liters of acetone. The desired product crystallizes out as the hydrochloride and is filtered off with suction and dried.

Yield: 1.98 g (×HCl×H$_2$O, 71%).
NMR (D$_2$O)

δ(ppm)=5.37 (1H, d, J=5 Hz, H-7); 5.16 (1H, d, J=5 Hz, H-6); 4.58 (1H, d, J=14 Hz, CH$_2$—pyrrol.); 3.99 (1H, d, J=14 Hz, CH$_2$—pyrrol.); 3.93 (1H, d, J=18 Hz, S—CH$_2$); 3.53 (1H, d, J=18 Hz, S—CH$_2$); 3.48 (4H, m, pyrrol.); 2.94 (3H, s,

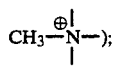

2.17 (4H, m, pyrrol.)

EXAMPLE 4

7-[1-(2-Aminothiazol-4-yl)-1(Z)-propenecarboxamido]-3-(1-methyl-1-pyrrolidinium)methyl-3-cephem-4-carboxylate 659 mg (3.58 mmol) of 1-(2-aminothiazol-4-yl-1(Z)-propenecarboxylic acid are dissolved in 4.5 ml of absolute dimethylformamide under nitrogen at room temperature. After addition of 230 μl of N-ethyldiisopropylamine, 250 μl of tripropylamine and 310 μl of tributylamine, the mixture is cooled to −50° C. 290 μl of methanesulphonyl chloride are added, and the solution is stirred at −50° C. for 30 min. This solution is then rapidly added to a solution, cooled to 0° C., of 900 mg (2.7 mmol) of 6-amino-3-(1-methyl-1-pyrrolinium)-methyl-3-cephem-4-carboxylate (×HCl×H$_2$O) in 1.4 ml of water and 1.4 ml of triethylamine. After 5 min, the reaction solution is poured into 400 ml of acetone. The resulting precipitate is filtered off with suction, dried and chromatographed on adsorber resin HP 20 (mobile phase: water/acetonitrile 95/5).

Yield: 530 mg (50.4%)
NMR (DMSO-d$_6$)

δ(ppm)=9.28 (1H, d, J=9 Hz, NH); 7.05 (2H, bs, NH$_2$); 6.35 (1H, q, J=8 Hz, C=CH); 6.23 (1H, s, thiazole); 5.68 (1H, dd, J=5 Hz, J=9 Hz, H-7-lactam); 5.17 (1H, d, J=5 Hz, H-6-lactam); 5.01 (1H, d, J=14 Hz, CH$_2$—pyrrol); 3.93 (1H, d, J=14 Hz, CH$_2$—pyrrol.); 3.83 (1H, d, J=18 Hz, S—CH$_2$); 3.45 (4H, m pyrrol.); 3.35 (1H, d, J=18 Hz, S—CH$_2$; 2.93 (3H, S,

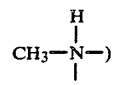

2.08 (4H, m, pyrrol.); 1.79 (3H, d, J=8 Hz, C=CH—CH$_3$);

EXAMPLE 5

7-Amino-3-(1-methyl-1-piperidinium)methyl-3-cephem-4-carboxylate 10 g (18.8 mmol) of benzhydryl 3-chloromethyl-7β-phenylacetamido-3-cephem-4-carboxylate are dissolved, at 0° C., in 112 ml of absolute methylene chloride. After addition of 56 ml of anisole and 56 ml of trifluoroacetic acid, the mixture is stirred at 0° C. for 25 minutes. It is evaporated in vacuo, 100 ml of benzene are added, and the mixture is evaporated under high vacuum for 1 h. The residue is dissolved in 100 ml of absolute tetrahydrofuran, and 9.3 g (94 mmol) of N-methylpiperidine are added. The solution is stirred at room temperature for 30 minutes. 100 ml of ether are added. The resulting precipitate is filtered off with suction, washed with 500 ml of ether and dissolved in 50 ml of water with the addition of NaHCO$_3$. Then 4 g of penicillin-G acylase are added and the pH is maintained constant at 7.8 by addition of 4N triethylamine in ethanol. After the enzymatic cleavage is complete, the acylase is removed by filtration and the filtrate is adjusted to pH 2 with concentrated hydrochloric acid. The resulting precipitate is removed by filtration through silica gel, and the filtrate is added dropwise to 2 liters of acetone. The desired product crystallizes out as hydrochloride and is filtered off with suction and dried.

Yield: 3.4 g (×HCl×H$_2$O, 49.5%)
NMR (D$_2$O)

δ(ppm)=5.40 (1H, d, J=5 Hz, H-7); 5.17 (1H, d, J=5 Hz, H-6); 4.66 (1H, d, J=14 Hz, CH$_2$-pip); 4.03 (1H, d, J=14 Hz, CH$_2$-pip); 3.97 (1H, d, J=18 Hz, S—CH$_2$); 3.54 (1H, d, J=18 Hz, S—CH$_2$); 3.34 (4H, m, pip); 2.98 (3H, s,

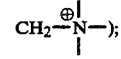

1.84 (4H, n, pip); 1.52 (2H, m, pip)

EXAMPLE 6

7-[1-(2-Aminothiazol-4-yl)-1(Z)-propenecarboxamido]-3-(1-methyl-1-piperidinium)methyl-3-cephem-4-carboxylate The preparation is carried out in analogy to Example 4, from 1-(2-aminothiazol-4-yl)-1(Z)-propenecarboxylic acid and 7-amino-3-(1-methyl-1-piperidinium)methyl-3-cephem-4-carboxylate.

$^1$H-NMR (DMSO-d$_6$)

δ(ppm)=9.32 (1H, d, J=9 Hz, NH); 7.07 (2H, bs, NH$_2$); 6.39 (1H, 9, J=8H, C=CH); 6.27 (1H, s, thiazole); 5.73 (1H, dd, J=5 Hz, J=9 Hz, H-7-lactam); 5.21 (1H, d, J=5 Hz, H-6-lactam), 5.12 (1H, d, J=14 Hz, CH$_2$-pip.); 3.98 (1H, d, J=14 Hz, CH$_2$-pip.); 3.88 (1H, d, J=18 Hz, S—CH$_2$); 3.42 (4H, m, pip); 3.39 (1H, d, J=18 Hz, S—CH$_2$); 2.98 (3H, S,

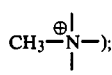

1.82 (7H, m, pip, C=C—CH3); 1.53 (2H, m, pip)

EXAMPLE 7

7-Amino-3-quinuclidiniummethyl-3-cephem-4-carboxylate 2.1 g (×HCl×H2O) of title compound are obtained from 10 g (18.2 mmol) of benzhydryl 3-chloromethyl-7β-phenylacetamido-3-cephem-4-carboxylate in analogy to Example 5.

NMR (D2O)

δ(ppm)=5.31 (1H, d, J=5 Hz); 5.11 (1H, d, J=5 Hz, H-6); 4.44 (1H, d, J=14 Hz, CH2—quin.); 3.85 (1H, d, J=14 Hz, CH2—quin.); 3.78 (1H, d, J=18 Hz, S—CH2); 3.42 (1H, d, J=18 Hz, S—CH2); 3.30 (6H, m, quin.); 2.07 (1H, m, quin); 1.90 (6H, m, quin)

EXAMPLE 8

7-[1-(2-Aminothiazol-4-yl)-1-(Z)-propenecarboxamido]-3-quinuclidiniummethyl-3-cephem-4-carboxylate The preparation was carried out in analogy to Example 4 from 1-(2-aminothiazol-4-yl)-1(Z)-propenecarboxylic acid and 7-amino-3-quinuclidiniummethyl-3-cephem-4-carboxylate.

1H-NMR (DMSO-d6)

δ(ppm)=9.28 (1H, d, J=9 Hz, NH); 7.04 (2H, bs, NH2); 6.35 (1H, q, J=8 Hz, C=CH); 6.23 (1H, s, thiazole); 5.70 (1H, dd, J=9 Hz, J=5 Hz, H-7-lactam), 5.17 (1H, d, J=5 Hz, H-6-lactam); 4.92 (1H, d, J=14 Hz, CH2-quin.); 3.81 (1H, d, J=18 Hz, S—CH2); 3.75 (1H, d, J=14 Hz, CH2—quin.); 3.38 (7H, m, S—CH2—quin.); 2.06 (1H, m, quin.); 1.85 (6H, m, quin); 1.80 (3H, d, J=8H, C=C—CH3);

EXAMPLE 9

3-(1-Methyl-1-pyrrolidinium)methyl-7β-phenylacetamido-3-cephem-4-carboxylate

Under nitrogen, 1.56 g (4 mmol) of 3-acetoxymethyl-7β-phenylacetamido-3-cephem-4-carboxylic acid are suspended at room temperature in 16 ml of absolute methylene chloride and induced to dissolve by the addition of 2.56 ml (12 mmol) of N-methyl-N-trimethylsilyl-trifluoroacetamide (MSTFA). After cooling to 0° C., 8 ml of a 2 molar solution of trimethylsilyl iodide in methylene chloride are added, and the reaction solution is stirred at 0° C. for 1 hour. After addition of 2.52 ml (30.8 mmol) of absolute tetrahydrofuran, the mixture is stirred at 0° C. for a further 15 minutes. Then 3.4 g (40 mmol) of N-methylpyrrolidine are added and the solution is stirred for 30 minutes. Then 0.8 ml of water and, after a further 5 minutes, 100 ml of absolute ether are added. The ether is decanted off, the residue is again stirred with ether, and after again decanting off, is dried in vacuo. Finally 100 ml of water is taken up and chromatographed on adsorber resin HP 20 (mobile phase: water/acetonitrile 95/5).

After freeze-drying the product fractions, 1.31 g (79%) of the product which is identical to the product prepared in Example 2 are obtained.

EXAMPLE 10

7-[Z-2-(2-aminothiazol-4-yl)-2-benzylideneacetamido]-3-(1-methyl-1-pyrrolidinium)methyl-3-cephem-4-carboxylate 0.4 g of 1-hydroxybenzotriazole and 0.6 g of N,N'-dicyclohexylcarbodiimide are added to a solution of 0.7 g of Z-2-(2-aminothiazol-4-yl)-2-benzylideneacetic acid in 10 ml of dimethylformamide, and the mixture is stirred at room temperature for four hours. The precipitated urea is removed by filtration with suction, and a solution of 0.8 g of 7-amino-3-(1-methyl-1-pyrrolidinium)methyl-3-cephem-4-carboxylate (×HCl×H2O) and 1.3 ml of triethylamine in 1.3 ml of water is added to the mother liquor. After stirring at room temperature for 4 hours, the reaction solution is stirred into 500 ml of acetone, and the precipitate which separates out is filtered off with suction and dried.

Yield: 0.43 g

NMR (D2O)

δ(ppm)=7.45 (5H, bs), 7.37 (1H, S), 6.70 (1H, s), 5.87 (1H, d, J=8 Hz), 5.35 (1H, J=14 Hz), 5.33 (1H, J=5 Hz), 4.05 (1H, J=14 Hz), 2.85 (1H, J=18 Hz), 4.03 (5H, m), 2.97 (3H, s), 2.22 (4H, m)

EXAMPLE 11

7-Amino-3-(4-methyl-4-morpholinium)methyl-3-cephem-4-carboxylate

The preparation is carried out in analogy to Example 5 from benzhydryl 3-chloromethyl-7β-phenylacetamido-3-cephem-4-carboxylate.

1H-NMR (D2O)

δ(ppm)=5.29 (1H, d, J=5 Hz, H-7-lactam); 5.07 (1H, d, J=5 Hz, H-6-lactam); 4.74 (1H, d, J=14 Hz, CH2—morph.);4.04 (1H, d, J=14 Hz, CH2—morph.); 3.92 (4H, m, morph.; 3.85 (1H, d, J=18 Hz, S—CH2); 3.46 (1H, d, J=18 Hz, S—CH2); 3.35 (4H, m, morph.); 3.05 m (3H, s,

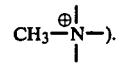

EXAMPLE 12

7-[1-(2-Aminothiazol-4-yl)-1(Z)-propenecarboxamido]-3-(4-methyl-4-morpholinium)methyl-3-cephem-4-carboxylate The preparation is carried out in analogy to Example 4 from 1-(2-aminothiazol-4-yl)-1(Z)-propenecarboxylic acid and 7-amino-3-(4-methyl-4-morpholinium)methyl-3-cephem-4-carboxylate.

1H-NMR (DMSO-D6)

δ(ppm)=9.28 (1H, d, J=9 Hz, NH); 7.03 (2H, bs, NH2); 6.35 (1H, q, J=8 Hz, C=C—H); 6.23 (1H, s, thiazole); 5.69 (1H, dd, J=9 Hz, J=5 Hz, H-7-lactam); 5.18 (2H, m, H-6-lactam, CH2—morph.); 3.80–4.10 (6H, m, CH2—morph., S—CH2, morph.); 3.30–3.50(5H, m, S—CH2, morph.); 3.07 (3H, S,

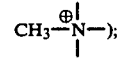

1.79 (3H, d, J=8 Hz, C═C—CH₃).

EXAMPLE 13

7-Amino-3-(trimethylammonium)methyl-3-cephem-4-carboxylate

The preparation is carried out in analogy to Example 5 from benzhydryl 3-chloromethyl-7β-phenylacetamido-3-cephem-4-carboxylate.

¹H-NMR (D₂O)

δ(ppm)=5.34 (1H, d, J=5 Hz, H-7-lactam); 5.12 (1H, d, J=5 Hz, H-6-lactam); 4.61 (1H, d, J=13 Hz, CH₂—ammon.); 3.97 (1H, d, J=13 Hz, CH₂—ammon.); 3.92 (1H, d, J=18 Hz, S—CH₂); 3.47 (1H, d, J=18 Hz, S—CH₂); 3.03 (9H, s,

).

EXAMPLE 14

7-[1-(2-Aminothiazol-4-yl)-1(Z)-propenecarboxamido]-3-(trimethylammonium)methyl-3-cephem-4-carboxylate The preparation is carried out in analogy to Example 4 from 1-(2-aminothiazol-4-yl)-1(Z)-propenecarboxylic acid and 7-amino-3-(trimethylammonium)methyl-3-cephem-4-carboxylate.

¹H-NMR (DMSO-d₆)

δ(ppm)=9.27 (1H, d, J=9 Hz, NH); 7.02 (2H, bs, NH₂); 6.33 (1H, q, J=8 Hz, C═C—H); 6.22 (1H, s, thiazole); 5.68 (1H, dd, J=9 Hz, J=5 Hz, H-7-lactam); 5.19 (1H, d, J=5 Hz, H-6-lactam); 5.00 (1H, d, J=13 Hz, —CH₂—ammon.); 3.91 (1H, d, J=13 Hz, CH₂—ammon.); 3.85 (1H, d, J=18 Hz, S—CH₂); 3.31 (1H, d, J=18 Hz, S—CH₂); 3.00 (9H, s, —N—); 1.79 (3H, d, J=8 Hz, C═C—CH₃).

EXAMPLE 15

7-Amino-3-(dimethylethylammonium)methyl-3-cephem-4-carboxylate

The preparation is carried out in analogy to Example 5 from benzhydryl 3-chloromethyl-7-phenylacetamido-3-cephem-4-carboxylate.

¹H-NMR (D₂O)

δ(ppm)=5.31 (1H, d, J=5 Hz, H-7-lactam); 5.10 (1H, d, J=5 Hz, H-6-lactam); 4.57 (1H, d, J=13 Hz, CH₂—ammon.); 3.89 (1H, d, J=13 Hz, CH₂—ammon.); 3.87 (1H, d, J=18 Hz, S—CH₂); 3.46 (1H, d, J=18 Hz, S—CH₂); 3.29

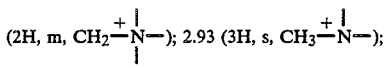

2.88 (3H, s, CH₃—N̈—);

1.25 (3H, t, J=7 HZ, CH₃).

EXAMPLE 16

7-[1-(2-Aminothiazol-4-yl)-1(Z)-propenecarboxamido]-3-(dimethylethylammonium)methyl-3-cephem-4-carboxylate The preparation is carried out in analogy to Example 4 from 1-(2-aminothiazol-4-yl)-1(Z)-propenecarboxylic acid and 7-amino-3-(dimethylethylammonium)methyl-3-cephem-4-carboxylate.

¹H-NMR (DMSO-d₆)

δ(ppm)=9.27 (1H, d, J=9 Hz, NH); 7.03 (2H, bs, NH₂); 6.33 (1H, q, J=8 Hz, C═C—H); 6.22 (1H, s, thiazole); 5.68 (1H, dd, J=9 Hz, J=5 Hz, H-7-lactam); 5.18 (1H, d, J=5 Hz, H-6-lactam); 5.05 (1H, d, J=13 Hz, CH₂—ammon.); 3.96 (1H, d, J=13 Hz, CH₂—ammon.); 3.94 (1H, d, J=18 Hz, S—CH₂); 3.36

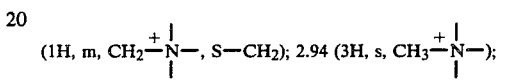

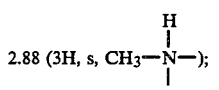

1.78 (3H, d, J=8 Hz, C═C—CH₃); 1.25 (3H, t, J=7 Hz, CH₃).

EXAMPLE 17

7-Amino-3-(1-ethyl-1-pyrrolidinium)methyl-3-cephem-4-carboxylate 10 g (18.8 mmol) of benzhydryl 3-chloromethyl-7β-phenylacetamido-3-cephem-4-carboxylate are dissolved, at 0° C., in 112 ml of absolute methylene chloride. After addition of 56 ml of anisole and 56 ml of trifluoroacetic acid, the mixture is stirred at 0° C. for 25 minutes. It is evaporated in vacuo, 100 ml of benzene are added, and the mixture is evaporated under high vacuum for 1 h. The residue is dissolved in 10 ml of absolute tetrahydrofuran, and 18.6 g (188 mmol) of N-ethylpyrrolidine are added. The solution is stirred at room temperature for 30 minutes. 100 ml of ethyl are added. The resulting precipitate is filtered off with suction, washed with 500 ml of ether and dissolved in 50 ml of water with the addition of NaHCO₃. Then 4 g of immobilized penicillin-G acylase are added and the pH is maintained constant at 7.8 by the addition of 4N triethylamine in ethanol. After the enzymatic cleavage is complete, the acylase is removed by filtration and the filtrate is adjusted to pH 2 with concentrated hydrochloric acid. The resulting precipitate is removed by filtration through silica gel with suction, and the filtrate is added dropwise to 2 liters of acetone. The desired product crystallizes out as the hydrochloride and is filtered off with suction and dried.

Yield: 1.76 g(×HCl×H₂O, 25.6%).

NMR (D₂O)

δ(ppm)=5.31 (1H, d, J=5 Hz, H-7-lactam); 5.12 (1H, d, J=5 HZ, H-6-lactam); 4.62 (1H, d, J=14 Hz, CH₂-pyrrol.), 3.88 (1H, d, J=14 Hz, CH₂—pyrrol.); 3.86 (1H, d, J=18 Hz, S—CH₂); 3.58 (1H, d, J=18 Hz, S—CH₂); 3.42 (4H, m, pyrrol.); 3.24 (2H, q, J=7 Hz,

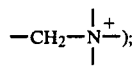

2.06 (4H, m, pyrrol.); 1.24 (3H, t, J=7 Hz, CH$_3$).

EXAMPLE 18

7-[1-(2-Aminothiazol-4-yl)-1(Z)-propenecarboxamido]-3-(1-ethyl-1-pyrrolidinium)methyl-3-cephem-4-carboxylate The preparation is carried out in analogy to Example 4 from 1-(2-aminothiazol-4-yl)-1(Z)-propenecarboxylic acid and 7-amino-3-(1-ethyl-1-pyrrolidinium)methyl-3-cephem-4-carboxylate.

$^1$H-NMR (DMSO-d$_6$)

δ(ppm)=9.27 (1H, d, J=9 Hz, NH); 7.02 (2H, bs, NH$_2$); 6.33 (1H, q, J=8 Hz, C═C—H); 6.22 (1H, s, thiazole); 5.67 (1H, dd, J=9 Hz, J=5 Hz, H-7-lactam); 5.15 (1H, d, J=5 Hz, H-6-lactam); 5.05 (1H, d, J=14 Hz, CH$_2$—pyrrol.); 3.83 (1H, d, J=14 Hz, CH$_2$—pyrrol.); 3.79 (1H, d, J=18 Hz, S—CH$_2$); 3.30–3.50 (7H, m); 2.00 (4H, m, pyrrol.); 1.79 (3H, d, J=8 Hz, C═C—CH$_3$); 1.26 (3H, t, J=7 Hz, CH$_3$).

EXAMPLE 19

3-[1-(2-Hydroxyethyl)-1-pyrrolidinium]methyl-7β-phenylacetamido-3-cephem-4-carboxylate Under nitrogen, 4.68 g (12 mmol) of 3-acetoxymethyl-7β-phenylacetamido-3-cephem-4-carboxylic acid is suspended, at room temperature, in 48 ml of absolute methylene chloride, and is dissolved by addition in 7.6 ml (36 mmol) of N-methyl-N-trimethylsilyltrifluoroacetamide (MSTFA). After cooling to 0° C., 7 ml (48 mmol) of trimethylsilyl iodide are added, and the reaction solution is stirred at 0° C. for 1 h. Then 14.4 ml (20 mmol) of N-(2-hydroxyethyl)pyrrolidine are added and the solution is stirred for 30 minutes. Then 2.4 ml of water are added and, after a further 5 minutes, the mixture is poured into 200 ml of ether. The ether is decanted off from the oily residue, the residue is again stirred with ether and, after renewed decantation, is taken up in water and chromatographed on adsorber resin HP 20 (eluting agent: acetonitrile/water 5/95).

Yield: 3.6 g (68%).

$^1$H-NMR (D$_6$-DMSO)

δ(ppm)=9.13 (1H, d, J=9 Hz, NH); 7.28 (5H, m, arom.); 5.55 (1H, dd, J=9 Hz, J=5 Hz, H-7-lactam); 5.06 (1H, d, J=5 Hz, H-6-lactam); 5.04 (1H, d, J=14 Hz, CH$_2$—pyrrol.); 3.95 (1H, d, J=14 Hz, CH$_2$—pyrrol.); 3.33–3.85 (12H, m); 2.04 (4H, m, pyrrol.).

EXAMPLE 20

7-Amino-3-[1-(2-hydroxyethyl)-1-pyrrolidinium]methyl-3-cephem-4-carboxylate 4 g of immobilized penicillin-G acylase are added to a solution of 3.5 g (7.8 mmol) of 3-[1-(2-hydroxyethyl)-1-pyrrolidinium]methyl-7β-phenylacetamido-3-cephem-4-carboxylate in 100 ml of water, and the pH is maintained constant at 7.8 by the addition of 4N triethylamine in ethanol. After the enzymatic cleavage is complete, the acylase is removed by filtration and the filtrate is adjusted to pH 2 with concentrated hydrochloric acid. The resulting precipitate is removed by filtration through silica gel with suction, and the filtrate is added dropwise to 2 liters of acetone. The desired product crystallizes out as the hydrochloride and is filtered off with suction and dried.

Yield: 1.9 g (×HCl×H$_2$O, 64%).

$^1$H-NMR (D$_6$-DMSO)

δ(ppm)=5.33 (1H, d, J=5 Hz, H-7-lactam); 5.13 (1H, d, J=5 Hz, H-6-lactam); 4.70 (1H, d, J=14 Hz, CH$_2$—pyrrol.); 3.93 (2H, m, CH$_2$—OH); 3.87 (1H, d, J=18 Hz, S—CH$_2$); 3.30–370 (7H, m); 2.11 (4H, m, pyrrol.).

EXAMPLE 21

7[-1-(2-Aminothiazol-4-yl)-1(Z)-propenecarboxamido]-3-[1-(2-hydroxyethyl)-1-pyrrolidinium]methyl-3-cephem-carboxylate The preparation is carried out in analogy to Example 4 from 1-(2-aminothiazol-4-yl)-1(Z)-propenecarboxylic acid and 7-amino-3-[1-(2-hydroxyethyl)-1-pyrrolidinium]methyl-3-cephem-4-carboxylate.

$^1$H-NMR (DMSO-d$_6$)

δ(ppm)=9.25 (1H, d, J=9 Hz); 7.00 (2H, bs, NH$_2$); 6.31 (1H, q, J=8 Hz, C═C—H); 6.19 (1H, s, thiazole); 5.65 (1H, dd, J=9 Hz, J=5 Hz, H-7-lactam); 5.14 (1H, d, J=5 Hz, H-6-lactam); 5.04 (1H, d, J=13 Hz, CH$_2$—pyrrol.); 3.80 (2H, m, CH$_2$—OH); 3.77 (1H, d, J=18 Hz, S—CH$_2$); 3.30–3.60 (7H, m); 2.01 (4H, m, pyrrol.); 1.76 (3H, d, J=8 Hz, C═C—CH$_3$).

EXAMPLE 22

3-[1-(2-Hydroxyethyl)-1-piperidinium]methyl-7-phenylacetamido-3-cephem-4-carboxylate The preparation is carried out in analogy to Example 19 from 3-acetoxymethyl-7β-phenylacetamido-3-cephem-4-carboxylic acid and N-(2-hydroxyethyl)piperidine.

$^1$H-NMR (D$_6$-DMSO)

δ(ppm)=9.17 (1H, d, J=9 Hz, NH); 7.30 (5H, m.arom.); 5.56 (1H, dd, J=9 Hz, J=5 Hz, H-7-lactam); 5.09 (1H, d, J=5 Hz, H-6-lactam); 5.08 (1H, d, J=13 Hz, CH$_2$—pip.); 3.10–3.90 (12H, m); 1.40–1.90 (6H, m).

EXAMPLE 23

7-Amino-3-[1-(2-hydroxyethyl)-1-piperidinium]methyl-3-cephem-4-carboxylate

The preparation is carried out in analogy to Example 20 from 3-[1-(2-hydroxyethyl)-1-piperidinium]methyl-7β-phenylacetamido-3-cephem-4-carboxylate.

$^1$H-NMR (D$_2$O)

δ(ppm)=5.34 (1H, d, J=5 Hz, H-7-lactam); 5.14 (1H, d, J=5 Hz, H-6-lactam); 4.75 (1H, d, J=14 Hz, CH$_2$—pip.); 3.96 (2H, m, CH$_2$—OH); 3.91 (1H, d, J=18 Hz, S—CH$_2$); 3.10–3.60 (7H, m); 1.40–1.90 (6H, m pip.).

EXAMPLE 24

7-[1-(2-Aminothiazol-4-yl)-1(Z)-propenecarboxamido]-3-[1-(2-hydroxyethyl)-1-piperidinium]methyl-3-cephem-4-carboxylate The preparation is carried out in analogy to Example 4 from 1-(2-aminothiazol-4-yl)-1(Z)-propenecarboxylic acid and 7-amino-3-[1-(2-hydroxyethyl)-1-piperidinium]methyl-3-cephem-4-carboxylate.

$^1$H-NMR (DMSO-D$_6$)

δ(ppm)=9.27 (1H, d, J=9 Hz, NH); 7.02 (2H, bs, NH$_2$); 6.33 (1H, q, J=8 Hz, C═C—H); 5.69 (1H, dd, J=9 Hz, J=5 Hz, H-7-lactam); 5.17 (1H, d, J=5 Hz, H-6-lactam); 5.09 (1H, d, J=13 Hz, CH$_2$—pip.); 4.00 (1H, d, J=13 Hz, CH$_2$—pip.); 3.82 (3H, m); 3.10–3.50

(7H, m); 1.40–1.90 (6H, m, Pip.); 1.78 (3H, d, J=8 Hz, C=C—CH₃).

EXAMPLE 25

3-[4-(2-Hydroxyethyl)-4-morpholinium]methyl-7β-phenylacetamido-3-cephem-4-carboxylate The preparation is carried out in analogy to Example 19 from 3-acetoxymethyl-7β-phenylacetamido-3-cephem-4-carboxylic acid and N-(2-hydroxyethyl)morpholine.

$^1$H-NMR (DMSO-d$_6$)

δ(ppm)=9.19 (1H, d, J=9 Hz, NH); 7.34 (5H, m, arom.); 5.62 (1H, dd, J=9 Hz, J=5 Hz, H-7-lactam); 5.20 (1H, d, J=14 Hz, CH₂—morph.); 5.13 (1H, d, J=5 Hz, H-6-lactam); 4.16 (1H, d, J=14 Hz, CH₂—morph.); 3.30–4.10 (16H, m).

EXAMPLE 26

7-Amino-3-[4-(2-hydroxyethyl)-4-morpholinium]methyl-3-cephem-4-carboxylate

The preparation is carried out in analogy to Example 20 from 3-[4-(2-hydroxyethyl)-4-morpholinium]methyl-7β-phenylacetamido-3-cephem-4-carboxylate.

$^1$H-NMR (D₂O)

δ(ppm)=5.36 (1H, d, J=5 Hz, H-7-lactam); 5.15 (1H, d, J=5 Hz, H-6-lactam); 4.88 (1H, d, J=14 Hz, CH₂—morph.); 4.21 (1H, d, J=14 Hz, CH₂—morph.); 3.30–4.10 (14H, m).

EXAMPLE 27

7-[1-(2-aminothiazol-4-yl)-1(Z)-propenecarboxamido]-3-[4-(2-hydroxyethyl)-4-morpholinium]methyl-3-cephem-4-carboxylate The preparation is carried out in analogy to Example 4 from 1-(2-aminothiazol-4-yl)-1(Z)-propenecarboxylic acid and 7-amino-3-[4-(2-hydroxyethyl)-4-morpholinium]methyl-3-cephem-4-carboxylate.

$^1$H-NMR (DMSO-d$_6$)

δ(ppm)=9.31 (1H, d, J=9 Hz, NH); 7.05 (2H, bs, NH₂); 6.37 (1H, q, J=8 Hz, C=C—H); 6.25 (1H, s, thiazole); 5.73 (1H, d, J=9 Hz, J=5 Hz, H-7-lactam); 5.21 (1H, d, J=5 Hz, H-6-lactam); 5.19 (1H, d, J=14 Hz, CH₂—morph.); 4.14 (1H, d, J=14 Hz, CH₂—morph.); 3.30–4.10 (14H, m); 1.81 (3H, d, J=8 Hz, C=C—H).

EXAMPLE 28

7-Amino-3-(1-ethyl-1-piperidinium)methyl-3-cephem-4-carboxylate

The preparation is carried out in analogy to Example 17 from benzhydryl 3-chloromethyl-7β-phenylacetamido-3-cephem-4-carboxylate and N-ethylpiperidine.

$^1$H-NMR (D₂O)

δ(ppm)=5.31 (1H, d, J=5 Hz, H-7-lactam); 5.10 (1H, d, J=5 Hz, H-6-lactam); 4.59 (1H, d, J=15 Hz, CH₂—pip.); 3.89 (1H, d, J=18 Hz, S—CH₂); 3.87 (1H, d, J=15 Hz, CH₂—pip.); 3.45 (1H, d, J=18 Hz, S—CH₂); 3.34 (2H, q, J=7 Hz,

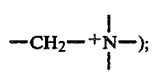

3.00–3.20 (4H, m, pip.); 1.40–1.70 (6H, m, pip.); 1.19 (3H, t, J=7 Hz, CH₃).

EXAMPLE 29

7-[1-(2-aminothiazol-4-yl)-1(Z)-propenecarboxamido]-3-(1-ethyl-1-piperidinium)methyl-3-cephem-4-carboxylate The preparation is carried out in analogy to Example 4 from 1-(2-aminothiazol-4-yl)-1(Z)-propenecarboxylic acid and 7-amino-3-(1-ethyl-1-piperidinium)methyl-3-cephem-4-carboxylate.

$^1$H-NMR (DMSO-d$_6$)

δ(ppm)=9.28 (1H, d, J=9 Hz, NH); 7.03 (2H, bs, NH₂); 6.35 (1H, q, J=8 Hz, C=CH); 6.23 (1H, s, thiazole); 5.69 (1H, dd, J=9 Hz, J=5 Hz, H-7-lactam); 5.19 (1H, d, J=5 Hz, H-6-lactam); 5.15 (1H, d, J=15 Hz, CH₂—pip.); 3.85 (2H, m, CH₂—pip., S—CH₂); 3.38 (5H, m, S—CH₂, pip.); 3.20 (2H,

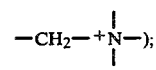

1.81 (3H, t, J=8 Hz, C=C—CH₃); 1.40–1.80 (6H, m, pip.); 1.22 (3H, t, J=7 Hz, CH₃).

EXAMPLE 30

7-Amino-3-(4-ethyl-4-morpholinium)methyl-3-cephem-4-carboxylate

The preparation is carried out in analogy to Example 17 from benzhydryl 3-chloromethyl-7β-phenylacetamido-3-cephem-4-carboxylate.

$^1$H-NMR (DMSO-d$_6$)

δ(ppm)=5.35 (1H, d, J=5 Hz, H-7-lactam); 5.16 (1H, d, J=5 Hz, H-6-lactam); 4.58 (1H, d, J=14 Hz, CH₂—morph.); 4.02 (1H, d, J=14 Hz, CH₂—morph.); 3.96 (4H, m, morph.); 3.90 (1H, d, J=18 Hz, S—CH₂); 3.30–3.60 (7H, m, S—CH₂, morph.,

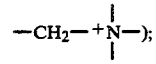

1.24 (3H, t, J=7 Hz, CH₃).

EXAMPLE 31

7-[1-(2-Aminothiazol-4-yl)-1(Z)-propenecarboxamido]-3-(4-ethyl-4-morpholinium)methyl-3-cephem-4-carboxylate The preparation is carried out in analogy to Example 4 from 1-(2-aminothiazol-4-yl)-1(Z)-propenecarboxylic acid and 7-amino-3-(4-ethyl-4-morpholinium)methyl-3-cephem-4-carboxylate.

$^1$H-NMR (DMSO-d$_6$)

δ(ppm)=9.26 (1H, d, J=9 Hz, NH); 7.01 (2H, bs, NH₂); 6.33 (1H, q, J=8 Hz, (C=C—H); 6.21 (1H, s, thiazole); 5.69 (1H, dd, J=9 Hz, J=5 Hz, H-7-lactam); 5.17 (2H, m, H-6-lactam, CH₂—morph.); 3.75–4.00 (6H, m. CH₂—morph., morph., S—CH₂; 3.10–3.70 (7H, morph.,

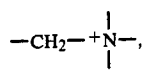

S—CH$_2$); 1.78 (3H, d, J=8 Hz, C=C—CH$_3$); 1.23 (3H, t, J=7 Hz, CH$_3$).

EXAMPLE 32

7-Amino-3-(1-propyl-1-pyrrolidinium)methyl-3-cephem-4-carboxylate

The preparation is carried out in analogy to Example 17 from benzhydryl 3-chloromethyl-7β-phenylacetamido-3-cephem-4-carboxylate and N-propylpyrrolidine.

$^1$H-NMR (D$_2$O)

δ(ppm)=5.33 (1H, d, J=5 Hz, H-7-lactam); 5.15 (1H, d, J=5 Hz, H-6-lactam); 4.63 (1H, d, J=13 Hz, CH$_2$—pyrrol.); 3.96 (1H, d, J=13 Hz, CH$_2$-pyrrol.); 3.88 (1H, d, J=18 Hz, S—CH$_2$); 3.55 (1H, d, J=18 Hz, S—CH$_2$); 3.45 (4H, m, pyrrol.); 3.12 (2H, m,

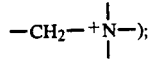

2.10 (4H, m, pyrrol.); 1.66 (2H, m, —CH$_2$); 0.85 (3H, m, CH$_3$).

EXAMPLE 33

7-[1-(2-Aminothiazol-4-yl)-1(Z)-propenecarboxamido]-3-(1-propyl-1-pyrrolidinium)methyl-3-cephem-4-carboxylate The preparation is carried out in analogy to Example 4 from 1-(2-aminothiazol-4-yl)-1(Z)-propenecarboxylic acid and 7-amino-3-(1-propyl-1-pyrrolidinium)methyl-3-cephem-4-carboxylate $^1$H-NMR δ(ppm)=9.25 (1H, d, J=9 Hz, NH); 7.02 (2H, bs, NH$_2$); 6.34 (1H, q, J=8 HZ, C=CH); 6.23 (1H, s, thiazole), 5.68 (1H, dd, J=9 Hz, J=5 Hz, H-7-lactam); 5.17 (1H, d, J=5 Hz, H-6-lactam; 5.08 (1H, d, J=13 Hz, CH$_2$—pyrrol.); 3.86 (1H, d, J=13 Hz, CH$_2$—pyrrol.); 3.81 (1H, d, J=18 Hz, S—CH$_2$); 3.40 (5H, m, pyrrol., S—CH$_2$); 3.12 (2H, m,

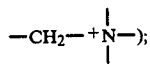

2.07 (4H, m, pyrrol.); 1.80 (5H, m, —CH$_2$—, C=C—CH$_3$); 0.91 (3H, t, J=7 Hz, CH$_3$).

EXAMPLE 34

7-Amino-3-(1-isopropyl-1-pyrrolidinium)methyl-3-cephem-4-carboxylate

The preparation is carried out in analogy to Example 17 from benzhydryl 3-chloromethyl-7β-phenylacetamido-3-cephem-4-carboxylate and N-isopropylpyrrolidine $^1$H-NMR (D$_2$O)

δ(ppm)=5.35 (1H, d, J=5 Hz, H-7-lactam); 5.13 (1H, d, J=5 Hz, H-6-lactam); 4.62 (1H, d, J=13 Hz, CH$_2$-pyrrol.) 4.02 (1H, d, J=13 Hz, CH$_2$—pyrrol.); 3.93 (1H, d, J=18 Hz, S—CH$_2$); 3.40-3.80 (6H, m, S—CH$_2$, pyrrol.,

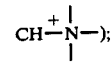

2.10 (4H, m, pyrrol.); 1.43 (6H, m, isoprop.).

EXAMPLE 35

7-[1-(2-Aminothiazol-4-yl)-1(Z)-propenecarboxamido]-3-(1-isopropyl-1-pyrrolidinium)methyl-3-cephem-4-carboxylate The preparation is carried out in analogy to Example 4 from 1-(2-aminothiazol-4-yl)-1(Z)-propenecarboxylic acid and 7-amino-3-(1-isopropyl-1-pyrrolidinium)methyl-3-cephem-4-carboxylate $^1$H-NMR (DMSO-d$_6$)

δ(ppm)=9.28 (1H, d, J=9 Hz, NH); 7.04 (2H, bs, NH$_2$); 6.37 (1H, q, J=8 Hz, C=CH); 6.25 (1H, s, thiazole); 5.70 (1H, dd, J=9 Hz, J=5 Hz, H-7-lactam); 5.20 (1H, d, J=5 Hz, H-6-lactam); 4.95 (1H, d, J=13 Hz, CH$_2$—pyrrol.); 3.93 (1H, d, J=13 Hz, CH$_2$—pyrrol.); 3.77 (1H, d, J=18 Hz, S—CH$_2$); 3.40-3.70 (6H, m,

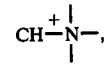

S—CH$_2$, S—CH$_2$, pyrrol.); 1.99 (4H, m, pyrrol.); 1.82 (3H, d, J=8 Hz, C=C—CH$_3$); 1.35 (6H, m, isoprop.).

EXAMPLE 36

7-Amino-3-(1-butyl-1-pyrrolidinium)methyl-3-cephem-4-carboxylate

The preparation is carried out in analogy to Example 17 from benzhydryl 3-chloromethyl-7β-phenylacetamido-3-cephem-4-carboxylate and N-butylpyrrolidine.

$^1$H-NMR (D$_2$O)

δ(ppm)=5.24 (1H, d, J=5 Hz, H-7-lactam); 5.04 (1H, d, J=5 Hz, H-6-lactam); 4.58 (1H, d, J=13 Hz, CH$_2$—pyrrol.); 3.85 (1H, d, J=13 Hz, CH$_2$—pyrrol.); 3.82 (1H, d, J=18 Hz, S—CH$_2$); 3.43 (1H, d J=18 Hz, S—CH$_2$); 3.28 (4H, m, pyrrol.); 3.07 (2H, m,

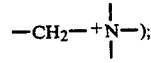

2.04 (4H, m, pyrrol.); 1.58 (2H, m, —CH$_2$—); 1.18 (2H, m, —CH$_2$—; 0.80 (3H, t, J=7 Hz, CH$_3$).

EXAMPLE 37

7-[1-(2-Aminothiazol-4-yl)-1(Z)-propenecarboxamido]-3-(1-butyl-1-pyrrolidinium)methyl-3-cephem-4-carboxylate The preparation is carried out in analogy to Example 4 from 1-(2-aminothiazol-4-yl)-1(Z)-propenecarboxylic acid and 7-amino-3-(1-butyl-1-pyrrolidinium)methyl-3-cephem-4-carboxylate.

$^1$H-NMR (DMSO-d$_6$)

δ(ppm)=9.24 (1H, d, J=9 Hz, NH); 6.98 (2H, bs, NH₂); 6.24 (1H, q, J=8 Hz, C=CH); 6.18 (1H, s, thiazole); 5.62 (1H, dd, J=9 Hz, J=5 Hz, H-7-lactam); 5.12 (1H, d, J=5 Hz, H-6-lactam); 5.01 (1H, d, J=13 Hz, CH₂—pyrrol.); 3.82 (1H, d, J=13 Hz, CH₂—pyrrol.); 3.76 (1H, d, J=18 Hz, S—CH₂); 3.30 (5H, m, S—CH₂, pyrrol.); 3.13 (2H, m,

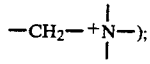

2.00 (4H, m, pyrrol.); 1.77 (3H, d, J=8 Hz, C=C—CH₃); 1.68 (2H, m, —CH₂—); 1.28 (2H, m, —CH₂—); 0.90 (3H, t, J=7 Hz, CH₃).

EXAMPLE 38

3-[1-(3-Hydroxypropyl)-1-pyrrolidinium]methyl-7-phenylacetamido-3-cephem-4-carboxylate The preparation is carried out in analogy to Example 19 from 3-acetoxymethyl-7β-phenylacetamido-3-cephem-4-carboxylic acid and N-(3-hydroxypropyl)pyrrolidine

¹H-NMR (D₆-DMSO)

δ(ppm)=9.16 (1H, d, J=9 Hz, NH); 7.30 (5H, arom.); 5.58 (1H, dd, J=9 Hz, J=5 Hz, H-7-lactam); 5.08 (1H, d, J=5 Hz, H-6-lactam); 5.03 (1H, d, J=13 Hz, CH₂—pyrrol.); 3.88 (1H, d, J=13 Hz, CH₂—pyrrol.) 3.84 (1H, d, J=18 Hz, S—CH₂); 2.90–3.60 (11H, m); 1.80–2.10 (6H, m).

EXAMPLE 39

7-Amino-3-[1-(3-hydroxypropyl)-1-pyrrolidinium]-methyl-3-cephem-4-carboxylate

The preparation is carried out in analogy to Example 20 from 3[1-(3-hydroxypropyl)-1-pyrrolidinium]methyl-3-cephem-4-carboxylate

¹H-NMR (D₂O)

δ(ppm)=5.31 (1H, d, J=5 Hz, H-7-lactam); 5.11 (1H, d, J=5 Hz, H-6-lactam); 4.63 (1H, d, J=13 Hz, CH₂—pyrrol.); 3.96 (1H, d, J=13 Hz, CH₂—pyrrol.); 3.88 (1H, d, J=18 Hz, S—CH₂); 3.40–3.60 (9H, m); 2.08 (4H, m, pyrrol.); 1.92 (2H, m, —CH₂).

EXAMPLE 40

7-[1-(2-Aminothiazol-4-yl)-1(Z)-propenecarboxamido]-3-[1-(3-hydroxypropyl)-1-pyrrolidinium]methyl-3-cephem-4-carboxylate The preparation is carried out in analogy to Example 4 from 1-(2-aminothiazol-4-yl)-1(Z)-propenecarboxylic acid and 7-amino-3-[1-(3-hydroxypropyl)-1-pyrrolidinium]methyl-3-cephem-4-carboxylate.

¹H-NMR (DMSO-d₆)

δ(ppm)=9.26 (1H, d, J=9 Hz, NH); 7.02 (2H, bs, NH₂); 6.34 (1H, q, J=8 Hz, C=CH); 6.23 (1H, s, thiazole); 5.70 (1H, dd, J=9 Hz, J=5 Hz, H-7-lactam); 5.16 (1H, d, J=5 Hz, H-6-lactam); 5.05 (1H, d, J=13 Hz, CH₂—pyrrol.); 4.84 (2H, m, CH₂—pyrrol., S—CH₂); 3.30–3.60 (9H, m, S—CH₂,

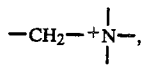

—CH₂—OH, pyrrol.); 2.07 (4H, m, pyrrol.); 1.88 (2H, m, —CH₂); 1.81 (3H, d, J=8 Hz, C=C—CH₃).

EXAMPLE 41

3-[1-[2-(2-Hydroxyethoxy)ethyl]-1-pyrrolidinium]-methyl-7β-phenylacetamido-3-cephem-4-carboxylate The preparation is carried out in analogy to Example 19 from 3-acetoxymethyl-7β-phenylacetamido-3-cephem-4-carboxylic acid and N-[2-(2-hydroxyethoxy)ethyl]pyrrolidine.

¹H-NMR (D₆-DMSO)

δ(ppm)=9.15 (1H, d, J=9 Hz, NH); 7.31 (5H, m, arom.); 5.57 (1H, dd, J=9 Hz, J=5 Hz, H-7-lactam); 5.15 (1H, d, J=13 Hz, CH₂—pyrrol.); 5.08 (1H, d, J=5 Hz, H-6-lactam); 3.99 (1H, d, J=13 Hz, CH₂—pyrrol.); 2.90–3.90 (14H, m); 2.08 (4H, m, pyrrol.);

EXAMPLE 42

7-Amino-3-[1-[2-(2-hydroxyethoxy)ethyl]-1-pyrrolidinium]methyl-3-cephem-4-carboxylate The preparation is carried out in analogy to Example 20 from 3-[1-[2-(2-hydroxyethoxy)ethyl]-b 1-pyrrolidinium]methyl-7β-phenylacetamido-3-cephem-4-carboxylate.

¹H-NMR (D₂O)

δ(ppm)=5.25 (1H, d, J=5 Hz, H-7-lactam); 5.07 (1H, d, J=5 Hz, H-6-lactam); 4.65 (1H, d, J=13 Hz, CH₂—pyrrol.) 4.04 (1H, d, J=13 Hz, CH₂—pyrrol.); 3.82 (1H, d, J=18 Hz, S—CH₂); 3.30–3.80 (9H, m); 2.05 (4H, m, pyrrol.).

EXAMPLE 43

7-[1-(2-Aminothiazol-4-yl)-1(Z)-propenecarboxamido]-3-[1-[2-(2-hydroxyethoxy)ethyl]-1-pyrrolidinium]methyl-3-cephem-4-carboxylate The preparation is carried out in analogy to Example 4 from 1-(2-aminothiazol-4-yl)-1(Z)-propenecarboxylic acid and 7-amino-3-[1-[2-(2-hydroxyethoxy)ethyl]-1-pyrrolidinium]methyl-3-cephem-4-carboxylate.

¹H-NMR (DMSO-d₆)

δ(ppm)=9.26 (1H, d, J=9 Hz, NH); 7.03 (2H, bs, NH₂); 6.34 (1H, q, J=8 Hz, C=CH); 6.23 (1H, s, thiazole); 5.69 (1H, dd, J=9 Hz, J=5 Hz, H-7-lactam); 5.17 (1H, d, J=5 Hz), H-6-lactam); 5.16 (1H, d, J=13 Hz, CH₂—pyrrol.); 3.98 (1H, d, J=13 Hz, CH₂—pyrrol.); 3.30–3.85 (14H, m); 2.06 (4H, m, pyrrol.); 1.81 (3H, d, J=8 Hz, C=C—CH₃).

EXAMPLE 44

3-[1-(2-Hydroxy-2-phenylethyl)-1-pyrrolidinium]methyl-7β-phenylacetamido-3-cephem-4-carboxylate The preparation is carried out in analogy to Example 19 from 3-acetoxymethyl-7β-phenylacetamido-3-cephem-4-carboxylic acid and DL-N-(2-hydroxy-2-phenylethyl)pyrrolidine. A mixture of two diastereoisomers is obtained.

¹H-NMR (D₆-DMSO)

δ(ppm)=9.14 (1H, d, J=9 Hz, NH); 7.20–7.60 (10H, m, arom.); 5.58 (1H, m, H-7-lactam); 5.33 (1H, m, CH—OH); 5.19 (1H, m, CH₂—pyrrol.); 5.07 (1H, d, J=5 Hz, H-6-lactam); 4.36 and 4.21 (1H, d, J=13 Hz, CH₂—pyrrol.); 3.10–3.90 (10H, m); 2.10 (4H, m, pyrrol.).

EXAMPLE 45

7-Amino-3-[1-(2-hydroxy-2-phenylethyl)-1-pyrrolidinium]methyl-3-cephem-4-carboxylate The preparation is carried out in analogy to Example 20 from 3-[1-(2-hydroxy-2-phenylethyl)-1-pyrrolidinium]methyl-3-cephem-4-carboxylate (mixture of two diastereoisomers).

$^1$H-NMR (D$_2$O)

δ(ppm)=7.40 (5H, bs, arom.); 5.30 (2H, m, H-7-lactam, CH—OH); 5.14 (1H, m, H-6-lactam); 4.82 (1H, m, CH$_2$—pyrrol.); 4.55 and 4.37 (1H, d, J=13 Hz, CH$_2$—pyrrol.); 3.30–4.00 (8H, m); 2.16 (4H, bs, pyrrol.).

EXAMPLE 46

7-[1-(2-Aminothiazol-4-yl)-1(Z)-propenecarboxamido]-3-[1-(2-hydroxy-2-phenylethyl)-1-pyrrolidinium]methyl-3-cephem-4-carboxylate The preparation is carried out in analogy to Example 4 from 1-(2-aminothiazol-4-yl)-1(Z)-propenecarboxylic acid and 7-amino-3-[1-(2-hydroxy-2-phenylethyl)-1-pyrrolidinium]methyl-3-cephem-4-carboxylate (mixture of two diastereoisomers).

$^1$H-NMR (DMSO-d$_6$)

δ(ppm)=9.24 (1H, d, J=9 Hz, NH); 7.30–7.50 (5H, m, arom.); 6.98 (2H, bs, NH$_2$); 6.31 (1H, q, J=8 Hz, C=CH); 6.20 and 6.21 (1H, s, thiazole); 5.66 (1H, m, H-7-lactam), 5.10–5.30 (3H, m, CH—OH, CH$_2$—pyrrol, H-6-lactam); 4.29 and 4.13 (1H, d, J=13 Hz, CH$_2$—pyrrol.); 3.20–3.85 (8H, m); 2.06 (4H, m, pyrrol.); 1.77 (3H, d, J=8 Hz, C=C—CH$_3$).

EXAMPLE 47

7-Amino-3-(diethylmethylammonium)methyl-3-cephem-4-carboxylate

The preparation is carried out in analogy to Example 5 from benzhydryl 3-chloromethyl-7β-phenylacetamido-3-cephem-4-carboxylate.

$^1$H-NMR (D$_2$O)

δ(ppm)=5.31 (1H, d, J=5 Hz, H-7-lactam), 5.11 (1H, d, J=5 Hz, H-6-lactam); 4.62 (1H, d, J=13 Hz, CH$_2$—ammon.); 3.88 (2H, m, CH$_2$—ammon., S—CH$_2$); 3.48 (1H, d, J=18 Hz, S—CH$_2$); 3.26

(4H, m, —CH$_2$—$\overset{+}{\underset{|}{N}}$—); 2.83 (3H, s, CH$_3$—$\overset{+}{\underset{|}{N}}$—);

1.24 (6H, m, CH$_3$).

EXAMPLE 48

7-[1-(2-Aminothiazol-b 4-yl)-1(Z)-propenecarboxamido]-3-(diethylmethylammonium)methyl-3-cephem-4-carboxylate The preparation is carried out in analogy to Example 4 from 1-(2-aminothiazol-4-yl)-1(Z)-propenecarboxylic acid and 7-amino-3-(diethylmethylammonium)methyl-3-cephem-4-carboxylate.

$^1$H-NMR (DMSO-D$_6$)

δ(ppm)=9.27 (1H, d, J=9 Hz, NH); 7.03 (2H, bs, NH$_2$); 6.34 (1H, q, J=8 Hz, C=C—H); 6.23 (1H, s, thiazole); 5.59 (1H, dd, J=9 Hz, J=5 Hz, H-7-lactam); 5.17 (1H, d,J=5 Hz, H-6-lactam); 5.11 (1H, d, J=13 Hz, CH$_2$—ammon.); 3.84 (2H, m, CH$_2$—ammon., S—CH$_2$); 3.20–3.50

(5H, m, S—CH$_2$, —CH$_2$—$\overset{+}{\underset{|}{N}}$—); 2.86 (3H, s, CH$_3$—$\overset{+}{\underset{|}{N}}$—);

1.80 (3H, d, J=8 Hz, C=C—CH$_3$); 1.24 (6H, m, CH$_2$).

EXAMPLE 49

7-Amino-3-(triethylammonium)methyl-3-cephem-4-carboxylate

The preparation is carried out in analogy to Example 5 from benzhydryl 3-chloromethyl-7β-phenylacetamido-3-cephem-4-carboxylate.

$^1$H-NMR (D$_2$O)

δ(ppm)=5.31 (1H, d, J=5 Hz, H-7-lactam); 5.13 (1H, d, J=5 Hz, H-6-lactam); 4.57 (1H, d, J=14 Hz, CH$_2$—ammon.); 3.89 (1H, d, J=18 Hz, S—CH$_2$); 3.88 (1H, d, J=14 Hz, CH$_2$—ammon.); 3.51 (1H, d, J=18 Hz, S—CH$_2$); 3.20 (6H, q, J=7 Hz, —CH$_2$—$\overset{+}{\underset{|}{N}}$—);

1.21 (9H, t, J=7 Hz, CH$_3$).

EXAMPLE 50

7-[1-(2-Aminothiazol-4-yl)-1(Z)-propenecarboxamido]-3-(triethylammonium)methyl-3-cephem-4-carboxylate The preparation is carried out in analogy to Example 4 from 1-(2-aminothiazol-4-yl)-1(Z)-propenecarboxylic acid and 7-amino-3-(triethylammonium)methyl-3-cephem-4-carboxylate.

$^1$H-NMR (DMSO-d$_6$)

δ(ppm)=9.29 (1H, d, J=9 Hz, NH); 7.06 (2H, bs, NH$_2$); 6.36 (1H, q, J=8 Hz, C=CH); 6.24 (1H, s, thiazole); 5.70 (1H, dd, J=9 Hz, H=5 Hz, H-7-lactam); 5.18 (1H, d, J=5 Hz, H-6-lactam); 5.13 (1H, d, J=13 Hz, CH$_2$—ammon.); 3.83 (2H, m, CH$_2$—ammon., S—CH$_2$); 3.20–3.50 (7H, m, S—CH$_2$, —CH$_2$—$\overset{+}{\underset{|}{N}}$—);

1.81 (3H, d, J=8 Hz, C=C—CH$_3$); 1.22 (9H, m, CH$_3$).

EXAMPLE 51

7-Amino-3-(N,N-dimethyl-N-2-hydroxyethylammonium)-methyl-3-cephem-4-carboxylate

The preparation is carried out in analogy to Example 5 from benzhydryl 3-chloromethyl-7β-phenylacetamido-3-cephem-4-carboxylate.

$^1$H-NMR (D$_2$O)

δ(ppm)=5.35 (1H, d, J=5 Hz, H-7-lactam); 5.13 (1H, d, J=5 Hz, H-6-lactam), 4.66 (1H, d, J=13 Hz, CH$_2$—ammon.) 4.08 (1H, d, J=13 Hz, CH$_2$—ammon.); 4.00 (2H, m, CH$_2$—OH); 3.93 (1H, d, J=18 Hz, S—CH$_2$); 3.51 (1H, d, J=18 Hz, S—CH$_2$);

3.46 (2H, m, —CH$_2$—$\overset{+}{\text{N}}$—); 3.09 (3H, s, CH$_3$—$\overset{+}{\text{N}}$—);

3.03 (3H, s, CH$_3$—$\overset{+}{\text{N}}$—).

EXAMPLE 52

7-[1-(2-Aminothiazol-4-yl)-1(Z)-propenecarboxamido]-3-(N,N-dimethyl-N-2-hydroxyethylammonium)methyl-3-cephem-4-carboxylate The preparation is carried out in analogy to Example 4 from 1-(2-aminothiazol-4-yl)-1(Z)-propenecarboxylic acid and 7-amino-3-(N,N-dimethyl-N-2-hydroxyethylammonium)methyl-3-cephem-4-carboxylate.

$^1$H-NMR (DMSO-d$_6$)

δ(ppm)=9.31 (1H, d, J=9 Hz, NH); 6.98 (2H, bs, NH$_2$); 6.31 (1H, q, J=8 Hz, C=CH); 6.19 (1H, s, thiazole); 5.65 (1H, dd, J=9 Hz, J=5 Hz, H-7-lactam); 5.13 (1H, d, J=5 Hz, H-6-lactam); 5.06 (1H, d, J=13 Hz, CH$_2$—ammon.); 3.85 (4H, m, CH$_2$—ammon., S—CH$_2$, CH$_2$—OH); 3.30–3.50

(3H, m, S—CH$_2$, —CH$_2$—$\overset{+}{\text{N}}$—); 3.02 (3H, s, CH$_3$—$\overset{+}{\text{N}}$—);

1.80 (3H, d, J=8 Hz, C=C—CH$_3$).

EXAMPLE 53

7-Amino-3-(N,N-diethyl-N-2-hydroxyethylammonium)-methyl-3-cephem-4-carboxylate

The preparation is carried out in analogy to Example 5 from benzhydryl 3-chloromethyl-7β-phenylacetamido-3-cephem-4-carboxylate.

$^1$H-NMR (D$_2$O)

δ(ppm)=5.33 (1H, d, J=5 Hz, H-7-lactam); 5.14 (1H, d, J=5 Hz, H-6-lactam), 4.69 (1H, d, J=13 Hz, CH$_2$—ammon.); 4.05 (1H, d, J=13 Hz, CH$_2$—ammon.); 3.96 (2H, m, CH$_2$—OH); 3.89 (1H, d, J=18 Hz, S—CH$_2$); 3.55 (1H, d, J=18 Hz, S—CH$_2$); 3.32 (6H, m, —CH$_2$—$\overset{+}{\text{N}}$—);

1.28 (6H, t, J=7 Hz, CH$_3$).

EXAMPLE 54

7-[1-(2-Aminothiazol-4-yl)-1(Z)-propenecarboxamido]-3-(N,N-diethyl-N-2-hydroxyethylammonium)methyl-3-cephem-4-carboxylate The preparation is carried out in analogy to Example 4 from 1-(2-aminothiazol-4-yl)-1(Z)-propenecarboxylic acid and 7-amino-3-(N,N-diethyl-N-2-hydroxyethylammonium)methyl-3-cephem-4-carboxylate.

$^1$H-NMR (DMSO-d$_6$)

δ(ppm)=9.26 (1H, d, J=9 Hz, NH); 7.01 (2H, bs, NH$_2$); 6.34 (1H, q, J=8 Hz, C=CH); 6.23 (1H, s, thiazole); 5.69 (1H, dd, J=9 Hz, J=5 Hz, H-7-lactam); 5.17 (1H, d, J=5 Hz, H-6-lactam); 5.10 (1H, d, J=13 Hz, CH$_2$—ammon.); 3.92 (1H, d, J=13 Hz, CH$_2$—ammon.); 3.81 (3H, m, CH$_2$OH, S—CH$_2$), 3.30–3.50 (7H, m, S—CH$_2$, —CH$_2$—$\overset{+}{\text{N}}$—);

1.81 (3H, d, J=8 Hz, C=C—CH$_3$); 1.26 (6H, m, CH$_3$).

EXAMPLE 55

7-Amino-3-(N,N-di-2-hydroxyethyl-N-methylammonium)methyl-3-cephem-4-carboxylate

The preparation is carried out in analogy to Example 5 from benzhydryl 3-chloromethyl-7β-phenylacetamido-3-cephem-4-carboxylate.

$^1$H-NMR (D$_2$O)

δ(ppm)=5.34 (1H, d, J=5 Hz, H-7-lactam); 5.12 (1H, d, J=5 Hz, H-6-lactam); 4.82 (1H, d, J=13 Hz, CH$_2$—ammon.); 4.15 (1H, d, J=13 Hz, CH$_2$—ammon.); 3.97 (5H, m, S—CH$_2$, CH$_2$OH); 3.20–3.60

(5H, S—CH$_2$; —CH$_2$—$\overset{+}{\text{N}}$—); 3.06 (3H, s, CH$_3$—$\overset{+}{\text{N}}$—).

EXAMPLE 56

7-[1-(2-Aminothiazol-4-yl)-1(Z)-propenecarboxamido]-3-(N,N-di-2-hydroxyethyl-N-methylammonium)methyl-3-cephem-4-carboxylate The preparation is carried out in analogy to Example 4 from 1-(2-aminothiazol-4-yl)-1(Z)-propenecarboxylic acid and 7-amino-3-(N,N-di-2-hydroxyethyl-N-methylammonium)methyl-3-cephem-4-carboxylate.

$^1$H-NMR (DMSO-d$_6$)

δ(ppm)=9.27 (1H, d, J=9 Hz, NH); 7.01 (2H, bs, NH$_2$); 6.33 (1H, q, J=8 Hz, C=CH); 5.68 (1H, dd, J=9 Hz, J=5 Hz, H-7-lactam); 5.17 (1H, d, J=5 Hz, H-6-lactam); 5.13 (1H, d, J=13 Hz, CH$_2$—ammon.); 4.03 (1H, d, J=12 Hz, CH$_2$—ammon.); 3.83 (5H, S—CH$_2$, CH$_2$OH); 3.20–3.60

(5H, S—CH$_2$, —CH$_2$—$\overset{+}{\text{N}}$—); 3.01 (3H, s, CH$_3$—$\overset{+}{\text{N}}$—);

1.80 (3H, d, J=8 Hz, C=C—CH$_3$).

EXAMPLE 57

7-Amino-3-(N,N-di-2-hydroxyethyl-N-ethylammonium)methyl-3-cephem-4-carboxylate

The preparation is carried out in analogy to Example 5 from 3-chloromethyl-7β-phenylacetamido-3-cephem-4-carboxylate.

$^1$H-NMR (D$_2$O)

δ(ppm)=5.36 (1H, d, J=5 Hz, H-7-lactam); 5.17 (1H, d, J=5 Hz, H-6-lactam); 4.84 (1H, d, J=14 Hz, CH$_2$—ammon.); 4.21 (1H, d, J=14 Hz, CH$_2$—ammon.); 3.94 (5H, m, S—CH$_2$, CH$_2$OH); 3.59 (1H, d, J=18 Hz, S—CH$_2$); 3.30–3.50 (6H, m,

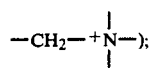

1.32 (3H, m, CH₃).

EXAMPLE 58

7-[1-(2-Aminothiazol-4-yl)-1(Z)-propenecarboxamido]-3-(N,N-di-2-hydroxyethyl-N-ethylammonium)methyl-3-cephem-4-carboxylate The preparation is carried out in analogy to Example 4 from 1-(2-aminothiazol-4-yl)-1(Z)-propenecarboxylic acid and 7-amino-3-(N,N-di-2-hydroxyethyl-N-ethylammonium)methyl-3-cephem-4-carboxylate.

¹H-NMR (DMSO-d₆)

δ(ppm)=9.26 (1H, d, J=9 Hz, NH); 7.01 (2H, bs, NH₂); 6.33 (1H, q, J=8 Hz, C═CH); 6.21 (1H, s, thiazole); 5.69 (1H, dd, J=9 Hz, J=5 Hz, H-7-lactam); 5.16 (1H, d, J=5 Hz, H-6-lactam); 5.09 (1H, d, J=13 Hz, CH₂—ammon.); 4.01 (1H, d, J=13 Hz, CH₂—ammon.); 3.80 (5H, m, S—CH₂, CH₂OH); 3.20–3.60 (7H, m, S—CH₂,

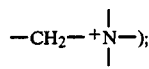

1.79 (3H, d, J=8 Hz, C═C—CH₃); 1.26 (3H, m, CH₃).

EXAMPLE 59

7-Amino-3-(N,N-dimethyl-N-2-methoxyethylammonium)methyl-3-cephem-4-carboxylate

The preparation is carried out in analogy to Example 5 from benzhydryl 3-chloromethyl-7β-phenylacetamido-3-cephem-4-carboxylate.

H-NMR (D₂O)

δ(ppm)=5.35 (1H, J=5 Hz, H-7-lactam); 5.13 (1H, d, J=5 Hz, H-6-lactam); 4.68 (1H, d, J=13 Hz, CH₂—ammon.); 4.03 (1H, d, J=13 Hz, CH₂—ammon.); 3.91 (1H, d, J=18 Hz, S—CH₂); 3.82 (2H, m, —CH₂—OCH₃); 3.50

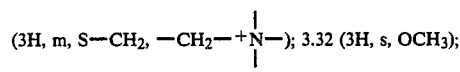

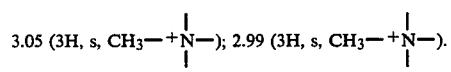

EXAMPLE 60

7-[1-(2-Aminothiazol-4-yl)-1(Z)-propenecarboxamido]-3-(N,N-dimethyl-N-2-methoxyethylammonium)methyl-3-cephem-4-carboxylate The preparation is carried out in analogy to Example 4 from 1-(2-aminothiazol-4-yl)-1(Z)-propenecarboxylic acid and 7-amino-3-(N,N-dimethyl-N-2-methoxyethylammonium)methyl-3-cephem-4-carboxylate.

¹H-NMR (DMSO-d₆)

δ(ppm)=9.26 (1H, d, J=9 Hz); 7.01 (2H, bs, NH₂); 6.32 (1H, q, J=8 Hz, C═CH); 6.21 (1H, s, thiazole); 5.68 (1H, dd, J=9 Hz, J=5 Hz, H-7-lactam); 5.17 (1H, d, J=5 Hz, H-6-lactam); 5.07 (1H, d, J=13 Hz, CH₂—ammon.); 3.95 (1H, d, J=13 Hz, CH₂—ammon.); 3.83 (1H, d, J=18 Hz, S—CH₂); 3.78 (2H, m, —CH₂—OCH₃); 3.30–3.60

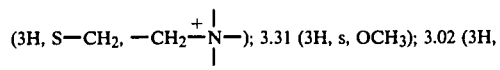3.31 (3H, s, OCH₃); 3.02 (3H,

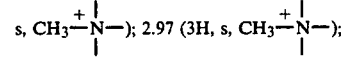

1.81 (3H, d, J=8 Hz, C═C—CH₃).

EXAMPLE 61

7-Amino-3-(N-benzyl-N,N-dimethyammonium)methyl-3-cephem-4-carboxylate

The preparation is carried out in analogy to Example 5 from benzhydryl 3-chloromethyl-7β-phenylacetamido-3-cephem-4-carboxylate.

¹H-NMR (D₂O)

δ(ppm)=7.38 (5H, m, arom.); 5.22 (1H, d, J=5 Hz, H-7-lactam); 5.00 (1H, d, J=5 Hz, H-6-lactam); 4.55 (1H, d, J=13 Hz, CH₂—ammon.); 4.33 (2H, m, CH₂—arom.); 3.91 (1H, d, J=13 Hz, CH₂—ammon.); 3.82 (1H, d, J=18 Hz, S—CH₂); 3.34 (1H, d, J=18 Hz, S—CH₂);

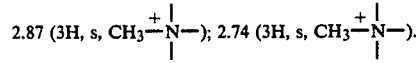

EXAMPLE 62

7-[1-(2-Aminothiazol-4-yl)-1(Z)-propenecarboxamido]-3-(N-benzyl-N,N-dimethylammonium)methyl-3-cephem-4-carboxylate The preparation is carried out in analogy to Example 4 from 1-(2-aminothiazol-4-yl)-1(Z)-propenecarboxylic acid and 7-amino-3-(N-benzyl-N,N-dimethylammonium)methyl-3-cephem-4-carboxylate.

¹H-NMR (DMSO-d₆)

δ(ppm)=9.29 (1H, d, J=9 Hz); 7.56 (5H, m, arom.) 7.03 (2H, bs, NH₂); 6.35 (1H, 1, J=8 Hz, C═CH); 6.24 (1H, s, thiazole); 5.71 (1H, dd, J=9 Hz, J=5 Hz, H-7-lactam); 5.23 (1H, d, J=5 Hz, H-6-lactam); 5.16 (1H, d, J=13 Hz, CH₂—ammon.); 4.56 (1H, d, J=12 Hz, —CH₂—arom.); 4.41 (1H, d, J=12 Hz, —CH₂—arom.); 4.03 (1H, d, J=13 Hz, CH₂—ammon.); 3.92 (1H, d, J=18 Hz, S—CH₂); 3.36 (1H, d, J=18 Hz, S—CH₂); 2.93

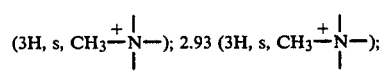

1.82 (3H, d, J=8 Hz, C═C—CH₃).

EXAMPLE 63

7-Amino-3-(N,N-dimethyl-N-furfurylammonium)methyl-3-cephem-4-carboxylate

The preparation is carried out in analogy to Example 5 from benzhydryl 3-chloromethyl-7β-phenylacetamido-3-cephem-4-carboxylate.

$^1$H-NMR (D$_2$O)

δ(ppm)=7.65 (1H, d, J=2 Hz, furyl); 6.80 (1H, J=3 Hz, furyl); 6.54 (1H, dd, J=2 Hz, J=3 Hz, furyl); 5.37 (1H, d, J=5 Hz, H-7-lactam); 5.15 (1H, d, J=5 Hz, H-6-lactam); 4.64 (1H, d, J=13 Hz, CH$_2$—ammon.); 4.54 (2H, m, CH$_2$—furyl); 4.03 (1H, d, J=13 Hz, CH$_2$—ammon.); 3.93 (1H, d, J=18 Hz, S—CH$_2$); 3.53 (1H, d, J=18 Hz, S—CH$_2$);

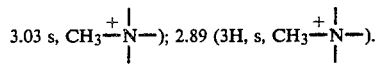

3.03 s, CH$_3$—$\overset{+}{N}$—); 2.89 (3H, s, CH$_3$—$\overset{+}{N}$—).

EXAMPLE 64

7-[1-(2-Aminothiazol-4-yl)-1(Z)-propenecarboxamido]-3-(N,N-dimethyl-N-furfurylammonium)methyl-3-cephem-4-carboxylate The preparation is carried out in analogy to Example 4 from 1-(2-aminothiazol-4-yl)-1(Z)-propenecarboxylic acid and 7-amino-3-(N,N-dimethyl-N-furfurylammonium)methyl-3-cephem-4-carboxylate.

$^1$H-NMR (DMSO-d$_6$)

δ(ppm)=9.27 (1H, d, J=9 Hz, NH); 7.91 (1H, d, J=2 Hz, furyl); 7.02 (2H, bs, NH$_2$); 6.90 (1H, d, J=3 Hz, furyl); 6.63 (1H, dd, J=2 Hz, J=3 Hz, furyl); 6.34 (1H, q, J=8 Hz, C=CH); 6.23 (1H, s, thiazole); 5.59 (1H, dd, J=9 Hz, J=5 Hz, H-7-lactam); 5.21 (1H, d, J=5 Hz, H-6-lactam); 5.06 (1H, d, J=13 Hz, CH$_2$—ammon.); 4.64 (1H, d, J=13 Hz, CH$_2$—furyl); 4.52 (1H, d, J=13 Hz, CH$_2$—furyl); 3.97 (1H, d, J=13 Hz, CH$_2$—ammon.); 3.87 (1H, d, J=18 Hz, S—CH$_2$); 3.34 (1H, d, J O 18 Hz, S—CH$_2$);

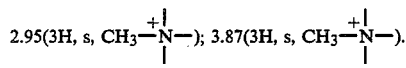

2.95(3H, s, CH$_3$—$\overset{+}{N}$—); 3.87(3H, s, CH$_3$—$\overset{+}{N}$—).

EXAMPLE 65

7-Amino-3-(N,N-dimethyl-N-3-formamidopropylammonium)methyl-3-cephem-4-carboxylate The preparation is carried out in analogy to Example 5 from benzhydryl 3-chloromethyl-7β-phenylacetamido-3-cephem-4-carboxylate.

$^1$H-NMR (D$_2$O)

δ(ppm)=8.04 (1H, s, CHO); 5.41 (1H, d, J=5 Hz, H-7-lactam); 5.18 (1H, d, J=5 Hz, H-6-lactam); 4.68 (1H, d, J=13 Hz, CH$_2$—ammon.); 4.03 (1H, d, J=13 Hz, CH$_2$—ammon.); 3.95 (1H, d, J=18 Hz, S—CH$_2$); 3.54 (1H, d, J=18 Hz, S—CH$_2$); 3.10–3.40 (4H, m);

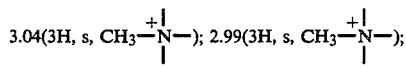

3.04(3H, s, CH$_3$—$\overset{+}{N}$—); 2.99(3H, s, CH$_3$—$\overset{+}{N}$—);

1.98 (2H, m).

EXAMPLE 66

7-[1-(2-Aminothiazol-4-yl)-1-(Z)-propenecarboxamido]-3-(N,N-dimethyl-N-3-formamidopropylammonium)methyl-3-cephem-4-carboxylate The preparation is carried out in analogy to Example 4 from 1-(2-aminothiazol-4-yl)-1(Z)-propenecarboxylic acid and 7-amino-3-(N,N-dimethyl-N-3-formamidopropylammonium)methyl-3-cephem-4-carboxylate.

$^1$H-NMR (DMSO-d$_6$)

δ(ppm)=9.26 (1H, d, J=9 Hz, NH); 8.05 (1H, s, CHO); 7.02 (2H, bs, NH$_2$); 6.34 (1H, q, J=8 Hz, C=CH); 6.22 (1H, s, thiazole); 5.69 (1H, dd, J=9 Hz, J=5 Hz, H-7-lactam); 5.19 (1H, d, J=5 Hz, H-6-lactam); 5.05 (1H, d, J=13 Hz, CH$_2$—ammon.); 4.90 (2H, m, CH$_2$—ammon., S—CH$_2$); 3.10–3.50 (5H, m); 2.97

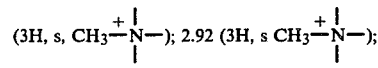

(3H, s, CH$_3$—$\overset{+}{N}$—); 2.92 (3H, s CH$_3$—$\overset{+}{N}$—);

1.90 (2H, m, —CH$_2$); 1.79 (3H, d, J=8 Hz, C=C—CH$_3$).

EXAMPLE 67

7-Amino-3-(4-hydroxy-1-methylpiperidinium)methyl-3-cephem-4-carboxylate

Under nitrogen, 1.56 g (4 mmol) of 3-acetoxymethyl-7β-phenylacetamido-3-cephem-4-carboxylic acid are suspended, at room temperature, in 16 ml of absolute methylene chloride, and induced to dissolve by addition of 2.56 ml (12 mmol) of N-methyl-N-trimethylsilyltrifluoroacetamide (MSTFA). After cooling to 0° C., 8 ml of a 2 molar solution of trimethylsilyl iodide in methylene chloride are added, and the reaction solution is stirred at 0° C. for 1 hour. After addition of 2.52 ml (30.8 mmol) of absolute tetrahydrofuran, the mixture is stirred at 0° C. for a further 15 minutes. Then 2.3 g (20 mmol) of 4-hydroxy-N-methylpiperidine are added, and the solution is stirred for 30 minutes. Then 0.8 ml of water and, after a further 5 minutes, 100 ml of absolute ether are added. The ether is decanted off, the residue is again stirred with ether and, after renewed decantation, the residue is dissolved in 50 ml of water with the addition of NaHCO$_3$. Then 4 g of penicillin-G acylase are added and the pH is maintained constant at 7.8 by addition of 4N triethylamine in ethanol. After the enzymatic cleavage is complete, the acylase is removed by filtration and the filtrate is adjusted to pH 2 with concentrated hydrochloric acid. The resulting precipitate is removed by filtration through silica gel with suction, and the filtrate is added dropwise to 2 liters of acetone. The desired product precipitates out as the hydrochloride and is filtered off with suction and dried.

875 mg (60%) of desired product are obtained as a mixture of two diastereoisomers.

$^1$H-NMR (D$_2$O)

δ(ppm)=5.49 (1H, d, J=5 Hz, H-7-lactam); 5.26 (1H, d, J=5 Hz, H-6-lactam); 4.80 (1H, m, CH$_2$—pip.); 4.16 (2H, m, CH$_2$—pip., CH—OH); 4.04 (1H, d, J=18 Hz, S—CH$_2$); 3.64 (1H, d, J=18 Hz, S—CH$_2$); 3.55 (2H, m, pip.); 3.38 (2H, m, pip.); 3.11 and 3.08 (3H, s,

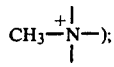

2.20 (2H, m, pip.); 1.95 (2H, m, pip.)

EXAMPLE 68

7-[1-(2-Aminothiazol-4-yl)-1(Z)-propenecarboxamido]-3-(4-hydroxy-1-methylpiperidinium)methyl-3-cephem-4-carboxylate The preparation is carried out in analogy to Example 4 from 1-(2-aminothiazol-4-yl)-1(Z)-propenecarboxylic acid and the mixture of diastereoisomers obtained in Example 67.

$^1$H-NMR (DMSO-d$_6$)

δ(ppm)=9.27 (1H, d, J=9 Hz, NH); 7.03 (2H, bs, NH$_2$); 6.36 (1H, q, J=8 Hz, C=CH); 6.24 (1H, s, thiazole); 5.70 (1H, dd, J=9 Hz, J=5 Hz, H-7-lactam), 5.19 (1H, d, J=5 Hz, H-6-lactam); 5.01 (1H, d, J=13 Hz, CH$_2$—pip.); 3.99 (1H, d, J=13 Hz, CH$_2$—pip.); 3.85 (2H, m, S—CH$_2$, CH—OH); 3.20–3.50 (5H, m, S—CH$_2$, pip.); 2.99 and 2.97 (3H, s,

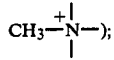

2.02 (2H, m, pip.); 1.83 (2H, d, J=8 Hz, C=C—CH$_3$); 1.77 (2H, m, pip.).

EXAMPLE 69

7-Amino-3-(4-hydroxymethyl-1-methylpiperidinium)-methyl-3-cephem-4-carboxylate

The preparation is carried out in analogy to Example 67 from 3-acetoxymethyl-7β-phenylacetamido-3-cephem-4-carboxylic acid and 4-hydroxymethyl-N-methylpiperidine.

$^1$H-NMR (D$_2$O)

δ(ppm)=5.30 [1]d, J=5 Hz, 5.10 [1]d, J=5 Hz, 4.60 [1]d, J=13 Hz, 4.01 [1]d, J=13 Hz, 3.88 [1]d, J=18 Hz, 3.10–3.65 [7]m, 2.92 [3]s, 1.40–1.95 [5]m.

EXAMPLE 70

7-[1-(2-Aminothiazol-4-yl)-1(Z)-propenecarboxamido]-3-(4-hydroxymethyl-1-methylpiperidinium)methyl-3-cephem-4-carboxylate The preparation is carried out in analogy to Example 4 from 1-(2-aminothiazol-4-yl)-1(Z)-propenecarboxylic acid and 7-amino-3-(4-hydroxymethyl-1-methylpiperidinium)methyl-3-cephem-4-carboxylate.

$^1$H-NMR (DMSO-d$_6$)

δ(ppm)=9.27 [1]d, J=9 Hz, 7.03 [2]bs, 6.35 [1]q, J=8 Hz, 6.34 [1]s, 5.69 [1]dd, J=9 Hz, J=5 Hz, 5,18 [1]d, J=5 Hz, 5.02 [1]d, J=13 Hz, 4,00 [1]d, J=13 Hz, 3.81 [1]d, J=17 Hz, 3.2–3.6 [8]m, 2.95 [3]s, 1.81 [3]d, J=8 Hz, 1.50–1.95 [5]m.

EXAMPLE 71

7-Amino-3-(4-formylaminomethyl-1-methylpiperidinium)methyl-3-cephem-4-carboxylate The preparation is carried out in analogy to Example 67 from 3-acetoxymethyl-7β-phenylacetamido-3-cephem-4-carboxylic acid and 4-formylaminomethyl-N-methylpiperidine.

$^1$H-NMR (D$_2$O)

δ(ppm)=8.09 [1]d, J=6 Hz, 5.18 [1]d, J=6 Hz, 4.65 [1]d, J=13 Hz, 4.11 [1]d, J=13 Hz, 3.95 [1]d, J=18 Hz, 3.20–3.75 [7]m, 3.03 [3]s, 1.60–2.10 [5]m.

EXAMPLE 72

7-[1-(2-Aminothiazol-4-yl)-1(Z)-propenecarboxamido]-3-(4-formylaminomethyl-1-methylpiperidinium)methyl-3-cephem-4-carboxylate The preparation is carried out in analogy to Example 4 from 1-(2-aminothiazol-4-yl)-1(Z)-propenecarboxylic acid and 7-amino-3-(4-formylaminomethyl-1-methylpiperidinium)methyl-3-cephem-4-carboxylate.

$^1$H-NMR (DMSO-d$_6$)

δ(ppm)=9.27 [1]d, J=9 Hz, 8.26 [1]bs, 8.08 [2]s, 7.02 [2]s, 6.34 [1]q, J=8 Hz, 6.24 [1]s, 5.70 [1]dd, J=9 Hz, J=5 Hz, 5.18 [1]d, J=5 Hz, 5.01 [1]d, J=13 Hz, 4.06 [1]d, J=13 Hz, 3.81 [1]d, J=17 Hz, 3.00–,360 [7]m, 2.93 [3]s, 1.80 [3]d, J=8 Hz, 1.75 [5]m.

EXAMPLE 73

7-Amino-3-(4-aminocarbonyl-1-methylpiperidinium)-methyl-3-cephem-4-carboxylate

The preparation is carried out in analogy to Example 67 from 3-acetoxymethyl-7β-phenylacetamido-3-cephem-4-carboxylic acid and 4-aminocarbonyl-N-methylpiperidine.

$^1$H-NMR (D$_2$O)

δ(ppm)=5.36 [1]d, J=5 Hz, 5.14 [1]d, J=5 Hz, 4.72 [1]d, J=13 Hz, 4.17 [1]d, J=13 Hz, 3.97 [1]d, J=16 Hz, 3.56 [1]d, J=16 Hz, 3.03 [3]s, 2.73 [1]m, 2.14 [4].

EXAMPLE 74

7-[1-(2-Aminothiazol-4-yl)-1(Z)-propenecarboxamido]-3-(4-aminocarbonyl-1-methylpiperidinium)methyl-3-cephem-4-carboxylate The preparation is carried out in analogy to Example 4 from 1-(2-aminothiazol-4-yl)-1(Z)-propenecarboxylic acid and 7-amino-3-(4-aminocarbonyl-1-methylpiperidinium)methyl-3-cephem-4-carboxylate.

$^1$H-NMR (DMSO-d$_6$)

δ(ppm)=9.24 [1]d, J=9 Hz, 7.47 [2]bs, 6.33 [1]q, J=8 Hz, 6.22 [1]s, 5.67 [1]dd, J=9 Hz, J=5 Hz, 5.15 [1]d, J=5 Hz, 5.00 [1]d, J=12 Hz, 3.99 [1]d, J=12 Hz, 3.80 [1]d, J=18 Hz, 3.20–3.60 [5]m, 2.96 [3]s, 2.42 [1]m, 1.83–2.30 [4]m, 1.82 [3]d, J=8 Hz.

EXAMPLE 75

7-Amino-3-(3-hydroxy-1-methylpiperidinium)methyl-3-cephem-4-carboxylate

The preparation is carried out in analogy to Example 67 from 3-acetoxymethyl-7β-phenylacetamido-3-cephem-4-carboxylic acid and 3-hydroxy-N-methylpiperidine.

A mixture of four diastereoisomers is obtained.

EXAMPLE 76

7-[1-2-Aminothiazol-4-yl-1(Z)-propenecarboxyamido]-3-(3-hydroxy-1-methylpiperidinium)methyl-3-cephem-4-carboxylate The preparation is carried out in analogy to Example 4 from the mixture of diastereomers obtained in Example 75 and 1-(2-aminothiazol-4-yl)1(Z)-propenecarboxylic acid.

A mixture of four diastereoisomers A-D is obtained, in the ratio A:B:C:D=1:2:1:2 (according to HPLC).

EXAMPLE 77

7-Amino-3-(2-hydroxymethyl-1-methylpiperidinium)-methyl-3-cephem-4-carboxylate

The preparation is carried out in analogy to Example 67 from 3-acetoxymethyl-7β-phenylacetamido-3-cephem-4-carboxylic acid and 2-hydroxymethyl-N-methylpiperidine.

A mixture of four diastereoisomers is obtained.

EXAMPLE 78

7-[1-(2-Aminothiazol-4-yl)-1(Z)-propenecarboxamido]-3-(2-hydroxymethyl-1-methylpiperidinium)methyl-3-cephem-4-carboxylate The preparation is carried out in analogy to Example 4 from the mixture of diastereoisomers obtained in Example 77 and 1-(2-aminothiazol-4-yl)-1(Z)-propenecarboxylic acid.

A mixture of four diastereoisomers A-D is obtained, in the ratio A:B:C:D=10:1:1:10.

The mixture can be separated by reversed phase chromatography.

EXAMPLE 79

7-Amino-3-[4-(3-hydroxypropyl]-1-methylpiperazinium)methyl-3-cephem-4-carboxylate The preparation is carried out in analogy to Example 67 from 3-acetoxymethyl-7β-phenylacetamido-3-cephem-4-carboxylic acid and N-(3-hydroxypropyl)-N'-methylpiperazine.

$^1$H-NMR (D$_2$O)

δ(ppm)=5.48 (1H, d, J=5 Hz, H-7-lactam); 5.27 (1H, d, J=5 Hz, H-6-lactam); 4.92 (1H, d, J=13 Hz, CH$_2$—pip.); 4.37 (1H, d, J=13 Hz, CH$_2$—pip.); 4.02 (1H, d, J=18 Hz, S—CH$_2$); 3.40–4.00 (13H, m); 3.32 (3H, s,

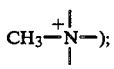

2.04 (2H, m, —CH$_2$).

EXAMPLE 80

7-[1-(2-Aminothiazol-4-yl)-1(Z)-propenecarboxamido]-3-[4-(3-hydroxypropyl)-1-methylpiperazinium]methyl-3-cephem-4-carboxylate The preparation is carried out in analogy to Example 4 from 1-(2-aminothiazol-4-yl)-1(Z)-propenecarboxylic acid and 7-amino-3-[4-(3-hydroxypropyl)-1-methylpiperazinium]methyl-3-cephem-4-carboxylate.

$^1$H-NMR (DMSO-d$_6$)

δ(ppm)=9.27 (1H, d, J=9 Hz, NH); 7.03 (1H, bs, NH$_2$); 6.33 (1H, q, J=8 Hz, C=CH); 6.22 (1H, s, thiazole); 5.56 (1H, dd, J=9 Hz, J=5 Hz, H-7-lactam); 5.17 (1H, d, J=13 Hz, CH$_2$—pip.); 4.00 (1H, d, J=13 Hz, CH$_2$—pip.); 3.83 (1H, d, J=18 Hz, S—CH$_2$); 3.20–3.50 (7H, m); 2.97 (3H, s,

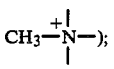

2.79 (2H, m); 2.45 (2H, m); 1.79 (3H, d, J=8 Hz, C=C—CH$_3$); 1.56 (2H, m, —CH$_2$).

EXAMPLE 81

7-Amino-3-(4-formyl-1-methylpiperazinium)methyl-3-cephem-4-carboxylate

The preparation is carried in analogy to Example 67 from 3-acetoxymethyl-7β-phenylacetamido-3-cephem-4-carboxylic acid and N-formyl-N'-methylpiperazine.

$^1$H-NMR (D$_2$O)

δ(ppm)=8.02 [1]s, 5.38 [1]d, J=5 Hz, 5.17 [1]d, J=5 Hz, 4.78 [1]d, J=13 Hz, 4.14 [2]d, J=13 Hz, 3.70–3.98 [3]m, 3.30–3.64 [6]m, 3.13 [3]s.

EXAMPLE 82

7-[1-(2-Aminothiazol-4-yl)-1(Z)-propenecarboxamido]-3-(4-formyl-1-methylpiperazinium)methyl-3-cephem-4-carboxylate The preparation is carried out in analogy to Example 4 from 1-(3-aminothiazol-4-yl)-1(Z)-propenecarboxylic acid and 7-amino-3-(4-formyl-1-methylpiperazinium)-methyl-3-cephem-4-carboxylate.

$^1$H-NMR (DMSO-d$_6$)

δ(ppm)=9.25 [1]d, J=9 Hz, 8.08 [1]s, 7.03 [1]q, J=8 Hz, 6.23 [1]s, 5.67 [1]dd, J=9 Hz, J=5 Hz, 5.17 [1]d, J=5 Hz, 5.15 [1]d, J=13 Hz, 4.03 [1]d, J=13 Hz, 3.20–3.95 [10]m, 3.08 [3]s, 1.89 [3]d, J=8 Hz.

EXAMPLE 83

7-Amino-3-(4-aminocarbonyl-1-methylpiperazinium)-methyl-3-cephem-4-carboxylate

The preparation is carried out in analogy to Example 67 from 3-acetoxymethyl-7β-phenylacetamido-3-cephem-4-carboxylic acid and N-aminocarbonyl-N'-methylpiperazine.

$^1$H-NMR (D$_2$O)

δ(ppm)=5.39 [1]d, J=5 Hz, 5.16 [1]d, J=5 Hz, 4.80 [1]d, J=13 Hz, 4.14 [1]d, J=13 Hz, 3.85–4.02 [3]m, 3.35–3.72 [7]m, 3.22 [3]s.

EXAMPLE 84

7-[1-(2-Aminothiazol-4-yl)-1(Z)-propenecarboxamido]-3-(4-aminocarbonyl-1-methylpiperazinium)methyl-3-cephem-4-carboxylate The preparation is carried out in analogy to Example 4 from 1-(2-aminothiazol-4-yl)-1(Z)-propenecarboxylic acid and 7-amino-3-(4-aminocarbonyl)-1-methylpiperazinium)methyl-3-cephem-4-carboxylate.

$^1$H-NMR (DMSO-d$_6$)

δ(ppm)=9.24 [1]d, J=9 Hz, 6.99 [2]bs, 6.31 [1]q; J=8 Hz, 6.30 [2]bs, 6.20 [1]s, 5.67 [1]dd, J=9 Hz, J=5 Hz, 5.15 [1]d, J=5 Hz, 5.09 [1]d, J=13 Hz, 3.99 [1]d, J=13 Hz, 3.78 [3]m, 3.10–3.65 [7]m, 3.00 [3]s, 1.78 [3]d, J=8 Hz.

EXAMPLE 85

7-Amino-3-(4-methylsulphonyl-1-methylpiperazinium)-methyl-3-cephem-4-carboxylate The preparation is carried out in analogy to Example 67 from 3-acetoxymethyl-7β-phenylacetamido-3-cephem-4-carboxylic acid and N-methylsulphonyl-N'-methylpiperazine.

$^1$H-NMR (D$_2$O)

δ(ppm)=5.39 [1]d, J=5 Hz, 5.17 [1]d, J=5 Hz, 4.78 [1]d, J=13 Hz, 4.14 [1]d, J=13 Hz, 3.92 [1]d, J=18 Hz, 3.40–3.80 [9]m, 3.10 [3]s, 3.06 [3]s.

EXAMPLE 86

7-[1-(2-Aminothiazol-4-yl)-1(Z)-propenecarboxamido]-3-(4-methylsulphonyl-1-methylpiperazinium)methyl-3-cephem-4-carboxylate The preparation is carried out in analogy to Example 4 from 1-(2-aminothiazol-4-yl)-1(Z)-propenecarboxylic acid and 7-amino-3-(4-methylsulphonyl-1-methylpiperazinium)methyl-3-cephem-4-carboxylate.

$^1$H-NMR (DMSO-d$_6$)

δ(ppm)=9.10 [1]d, J=9 Hz, 7.02 [2]bs, 6.33 [1]q, J=8 Hz, 6.21 [1]s, 5.69 [1]dd, J=9 Hz, J=5 Hz, 5.15 [1]d, J=5 Hz, 5.13 [1]d, J=13 Hz, 4.08 [1]d, J=13 Hz, 3.83 [1]d, J=18 Hz, 3.20–3.73 [9]m, 3.05 [3]s, 3.03 [3]s, 1.80 [3]d, J=8 Hz.

EXAMPLE 87

7-Amino-3-(4-dimethylaminosulphonyl-1-methylpiperazinium)methyl-3-cephem-4-carboxylate The preparation is carried out in analogy to Example 67 from 3-acetoxymethyl-7β-phenylacetamido-3-cephem-4-carboxylic acid and N-dimethylaminosulphonyl-N'-methylpiperazine.

$^1$H-NMR (D$_2$O)

δ(ppm)=5.39 [1]d, J=5 Hz, 5.16 [1]d, J=5 Hz, 4.82 [1]d, J=13 Hz, 4.18 [1]d, J=13 Hz, 3.98 [1]d, J=18 Hz, 3.48–3.80 [9]m, 3.13 [3]s, 2.89 [6]s.

EXAMPLE 88

7-[1-(2-Aminothiazol-4-yl)-1(Z)-propenecarboxamido]-3-(4-dimethylaminosulfonyl-1-methylpiperazinium)-methyl-3-cephem-4-carboxylate The preparation is carried out in analogy to Example 4 from 1-(2-aminothiazol-4-yl)-propenecarboxylic acid and 7-amino-3-(4-dimethylaminosulphonyl-1-methylpiperazinium)methyl-3-cephem-4-carboxylate.

$^1$H-NMR (DMSO-d$_6$)

δ(ppm)=9.25 [1]d, J=9 Hz, 7.00 [2]bs, 6.32 [1]q, J=8 Hz, 6.20 [1]s, 5.68 [1]dd, J=9 Hz, J=5 Hz, 5.16 [1]d, J=5 Hz, 5.14 [1]d, J=13 Hz. 4.05 [1]d, 3.81 [1]d, J=18 Hz, 3.20–3.70 [9]m, 3.04 [3]s, 2.80 [6]s.

EXAMPLE 89

7-Amino-3-(1,4-dimethyl-3-oxopiperazinium)methyl-3-cephem-4-carboxylate

The preparation is carried out in analogy to Example 67 from 3-acetoxymethyl-7β-phenylacetamido-3-cephem-4-carboxylic acid and 1,4-dimethyl-3-oxopiperazine. A mixture of 2 isomers is obtained.

$^1$H-NMR (D$_2$O)

δ(ppm)=5.40 und 5.39 [1]d, J=5 Hz, 5.19 und 5.18 [1]d, J=5 Hz, 4.86 und 4.76 [1]d, J=13 Hz, 4.24 und 4.21 [1]d, J=13 Hz, 4.24 [1]d, J=18 Hz, 4.06 [1]m, 3.62–4.00 [5]m, 3.56 und 3.54 [1]d, J=18 Hz, 3.17 und 3.15 [3]s, 2.98 [3]s.

EXAMPLE 90

7-[1-(2-Aminothiazol-4-yl)-1(Z)-propenecarboxamido]-3-(1,4-dimethyl-3-oxopiperazinium)methyl-3-cephem-4-carboxylate The preparation is carried out in analogy to Example 4 from 1-(2-aminothiazol-4-yl)-1(Z)-propenecarboxylic acid and 7-amino-3-(1,4-dimethyl-3-oxopiperazinium)-methyl-3-cephem-4-carboxylate (mixture of 2 isomers).

$^1$H-NMR (DMSO-d$_6$)

δ(ppm)=9.29 [1]bd, J=9 Hz, 7.02 [2]bs, 6.35 [1]q, J=8 Hz, 6.24 [1]s, 5.72 [1]dd, J=9 Hz, J=5 Hz, 5.19 und 5.18 [1]d, J=5 Hz, 5.08 und 5.04 [1]d, J=13 Hz, 4.33 und 4.12 [1]d, J=13 Hz, 3.20–4.20 [8]m, 3.08 [3]bs, 2.92 [3]bs, 1.82 [3]d, J=8 Hz.

It will be understood that the specification and examples are illustrative but not limitative of the present invention and that other embodiments within the spirit and scope of the invention will suggest themselves to those skilled in the art.

I claim:

1. A β-lactam compound of the formula

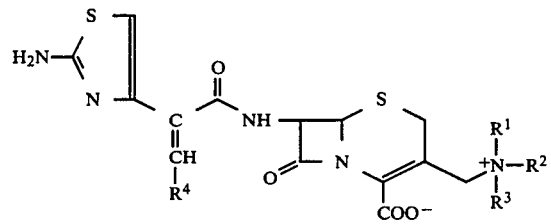

in which
R$^1$, R$^2$ and R$^3$ each independently is a C$_1$–C$_6$-aliphatic radical optionally substituted by hydroxyl, amino, carboxy, cyano, nitro, C$_1$–C$_6$-alkoxy, C$_1$–C$_6$-alkoxycarbonyl or halo, or in which R$^1$ has the aforementioned meaning, and R$^2$ and R$^3$ together with the N atom, form a pyrrolidinium, piperidinium, piperazinium, morpholinium, pyrrolinium, pyrazolidinium, indolinium, isoindolinium, oxazolidinium, thiazolidinium or thiomorpholinium radical which is optionally substituted by C$_1$–C$_6$-alkyl which itself is optionally substituted by hydroxyl, carboxyl, cyano, nitro, amino, halogen, C$_1$–C$_6$-alkoxy, C$_1$–C$_6$-alkoxycarbonyl, formyl, C$_1$–C$_6$-alkoxycarbonyl, carbamyl, sulpho, C$_1$–C$_6$-alkylamino and dialkylamino, C$_1$–C$_6$-alkylcarbonylamino, C$_1$–C$_6$-alkylthio, C$_1$–C$_6$-alkylsulphinyl, C$_1$–C$_6$-alkylsulphonyl, phenyl, naphthyl or pyridyl, and R$^4$ is a lower alkyl radical, lower cycloalkyl radical, phenyl, dichlorophenyl, trichlorophenyl, hydroxycarbonylphenyl, hydroxycarbonyl-C$_1$–C$_6$-alkylphenyl, pyridyl, aminothiazolyl, hydroxycarbonyl, hydroxycarbonyl-C$_1$–C$_4$-alkyl, lower alkoxycarbonyl or C$_1$–C$_4$-alkylsulphonyl.

2. A β-lactam compound according to claim 1, wherein any of R$^1$, R$^2$ and R$^3$ which is a substituted aliphatic radical is a substituted C$_1$–C$_6$-alkyl radical.

3. A β-lactam compound according to claim 1, in which R$^4$ is a lower alkyl radical or hydroxycarbonyl-C$_1$–C$_4$-alkyl.

4. A β-lactam compound according to claim 1 of the Z configuration, in which

R$^1$, R$^2$ and R$^3$ each independently represents methyl, ethyl, propyl, cyclopropyl, cyclopropylmethyl, cyclopentyl, cyclopentylmethyl, hydroxymethyl, hydroxyethyl, hydroxypropyl, aminomethyl, aminoethyl, hydroxycarbonylmethyl, hydroxycarbonylethyl, cyanomethyl, nitromethyl, nitroethyl, methoxymethyl, methoxycarbonylmethyl or trifluoromethyl, and R$^4$ denotes methyl, ethyl, propyl, cyclopropyl or cyclopentyl, phenyl, dichlorophenyl, trichlorophenyl, hydroxycarbonylphenyl, hydroxycarbonyl-$C_1$-$C_6$-alkylphenyl, pyridyl, aminothiazolyl, hydroxycarbonyl, 1-hydroxy-carbonyl-1-methylethyl, methoxycarbonyl or methylsulphonyl.

5. A compound according to claim 1, wherein such compound is 7-[1-(2-aminothiazol-4-yl)-1(Z)-propenecarboxamido]-3-(1-methyl-1-pyrrolidinium)methyl)-3-cephem-4-carboxylate.

6. A compound according to claim 1, wherein such compound is 7-[1-(2-aminothiazol-4-yl)-1(Z)-propenecarboxamido]-3-(4-hydroxy-1-methylpiperidinium)methyl-3-cephem-4-carboxylate.

7. A compound according to claim 1, wherein such compound is 7-[1-(2-aminothiazol-4-yl)-1(Z)-propenecarboxamido]-3-(4-aminocarbonyl-1-methylpiperidinium)methyl-3-cephem-4-carboxylate.

8. A compound according to claim 1, wherein such compound is 7-[1-(2-aminothiazol-4-yl)-1(Z)-propenecarboxamido]-3-(2-hydroxymethyl-1-methylpiperidinium)methyl-3-cephem-4-carboxylate.

9. A compound according to claim 1, wherein such compound is 7-[1-(2-aminothiazol-4-yl)-1(Z)-propenecarboxamido]-3-(4-aminocarbonyl-1-methylpiperazinium)methyl-3-cephem-4-carboxylate.

10. An antibacterial composition comprising an antibacterially effective amount of a compound according to claim 1 in admixture with a diluent.

11. A unit dose of a composition according to claim 10 in the form of a tablet, capsule or ampule.

12. A method of combating bacteria which comprises applying to the bacteria or a bacterial habitat an antibacterially effective amount of a compound according to claim 1.

13. The method according to claim 12, wherein such compound is

7-[1-(2-aminothiazol-4-yl)-1(Z)-propenecarboxamido]-3-(1-methyl-1-pyrrolidinium)methyl-3-cephem-4-carboxylate, 7-[1-(2-aminothiazol-4-yl)-1(Z)-propenecarboxamido]-3-(4-hydroxy-1-methylpiperidinium)methyl-3-cephem-4-carboxylate, 7-[1-(2-aminothiazol-4-yl)-1(Z)-propenecarboxamido]-3-(4-aminocarbonyl-1-methylpiperidinium)methyl-3-cephem-4-carboxylate, 7-[1-(2-aminothiazol-4-yl)-1(Z)-propenecarboxamido]-3-(2-hydroxymethyl-1-methylpiperidinium)methyl-3-cephem-4-carboxylate or 7-[1-(2-aminothiazol-4-yl)-1(Z)-propenecarboxamido]-3-(4-aminocarbonyl-1-methylpiperazinium)methyl-3-cephem-4-carboxylate.

* * * * *